(12) United States Patent
Haag et al.

(10) Patent No.: US 11,041,090 B2
(45) Date of Patent: Jun. 22, 2021

(54) AMPHIPHILIC BLOCK COPOLYMER AND COATING ARRANGEMENT

(71) Applicant: FREIE UNIVERSITÄT BERLIN, Berlin (DE)

(72) Inventors: Rainer Haag, Berlin (DE); Marie Weinhart, Berlin (DE); Qiang Wei, Stuttgart (DE); Leixiao Yu, Berlin (DE)

(73) Assignee: FREIE UNIVERSITÄT BERLIN, Berlin (DE)

( * ) Notice: Subject to any disclaimer, the term of this patent is extended or adjusted under 35 U.S.C. 154(b) by 197 days.

(21) Appl. No.: 16/314,630

(22) PCT Filed: Jun. 30, 2017

(86) PCT No.: PCT/EP2017/066313
§ 371 (c)(1),
(2) Date: Dec. 31, 2018

(87) PCT Pub. No.: WO2018/002322
PCT Pub. Date: Jan. 4, 2018

(65) Prior Publication Data
US 2019/0169463 A1 Jun. 6, 2019

(30) Foreign Application Priority Data
Jun. 30, 2016 (EP) .................................... 16177279

(51) Int. Cl.
| | | |
|---|---|---|
| C09D 171/02 | (2006.01) | |
| C12M 1/00 | (2006.01) | |
| C08G 83/00 | (2006.01) | |
| C09D 201/00 | (2006.01) | |
| C08G 65/00 | (2006.01) | |
| C09D 201/06 | (2006.01) | |
| C09D 201/02 | (2006.01) | |
| C08G 65/22 | (2006.01) | |
| C08G 65/334 | (2006.01) | |
| C09D 5/00 | (2006.01) | |

(52) U.S. Cl.
CPC ........... *C09D 171/02* (2013.01); *C08G 65/00* (2013.01); *C08G 65/22* (2013.01); *C08G 65/3348* (2013.01); *C08G 83/00* (2013.01); *C09D 5/00* (2013.01); *C09D 201/00* (2013.01); *C09D 201/02* (2013.01); *C09D 201/025* (2013.01); *C09D 201/06* (2013.01); *C12M 23/20* (2013.01); *C08G 2150/00* (2013.01); *C08G 2650/10* (2013.01); *C08G 2650/54* (2013.01)

(58) Field of Classification Search
CPC .............. C08G 83/006; C08G 2650/00; C08G 2650/10; C08G 2650/54; C08G 2150/00; C08G 83/00; C08G 65/00; C08G 65/22; C08G 65/3348; C08L 101/005; C08J 7/042; C08J 2300/202; C09D 5/00; C09D 5/1693; C09D 171/00; C09D 171/02; C09D 201/00; C09D 201/02; C09D 201/005; C09D 201/025; C09D 201/06; A61L 2420/08; A61L 27/34; A61F 2002/009; A61F 2/0077; C12M 23/20
See application file for complete search history.

(56) References Cited

U.S. PATENT DOCUMENTS

| | | | |
|---|---|---|---|
| 5,858,653 A | 1/1999 | Duran et al. | |
| 6,444,318 B1 | 9/2002 | Guire et al. | |
| 2014/0271774 A1 | 9/2014 | Drumheller et al. | |
| 2016/0222224 A1* | 8/2016 | Haag ..................... | A61F 2/0077 |

FOREIGN PATENT DOCUMENTS

| | | |
|---|---|---|
| WO | 97/16544 A1 | 5/1997 |
| WO | 99/47176 A2 | 9/1999 |
| WO | 03/008646 A2 | 1/2003 |
| WO | 2015/036364 A1 | 3/2015 |
| WO | 2018/002322 A2 | 1/2018 |

OTHER PUBLICATIONS

Burnett, G. M., Block and Graft Copolymers, Annu. Rev. Phys. Chem., 10, pp. 103-122, 1959. (Year: 1959).*
Dalsin, L. J., and Messersmith, B., P., "Bioinspired antifouling polymers," Materials Today, vol. 8, Issue 9, pp. 38-46 (Sep. 2005).
European Search Report dated Dec. 8, 2016 as received in Application No. 16 17 7279.
Lee, H., et al., "Mussel-Inspired Surface Chemistry for Multifunctional Coatings," Science, vol. 318, Issue 5849, pp. 426-430 (Oct. 19, 2007).
Li, Z., and Chau, Y., "Synthesis of Linear Polyether Polyol Derivatives As New Materials for Bioconjugation," Bioconjugate Chemistry, vol. 20, Issue 4, pp. 780-789 (2009).
Niederer, K., et al., Catechol Acetonide Glycidyl Ether (CAGE): A Functional Epoxide Monomer for Linear and Hyperbranched Multi-Catechol Functional Polyether Architectures, Macromolecules, vol. 49, Issue 5, pp. 1655-1665 (Feb. 2016).
Wei Q., et al., Multivalent Anchoring and Cross-Linking of Mussel Inspired Antifouling Surface Coatings, Biomacromolecules, vol. 15, pp. 3061-3071 (2014).

(Continued)

*Primary Examiner* — Christopher M Rodd
(74) *Attorney, Agent, or Firm* — Maschoff Brennan

(57) ABSTRACT

The disclosure relates to an amphiphilic block copolymer comprising a first block consisting of a polymeric hydrophilic domain, wherein the polymeric hydrophilic domain consists of a polyglycerol; an optional second block consisting of a hydrophobic domain and a first linker domain, wherein the second block is covalently bound to the first block via the first linker domain, an optional third block consisting of a catechol domain and a second linker domain, wherein the third block is covalently bound to the first block via the second linker domain; and a fourth block consisting of a crosslinking domain and a third linker domain, wherein the fourth block is covalently bound to the first block via the third linker domain, wherein the crosslinking domain comprises a reactive residue enabling a crosslinking between individual molecules of the amphiphilic block copolymer.

13 Claims, 14 Drawing Sheets

(56) References Cited

OTHER PUBLICATIONS

Wei, Q., et al., A Universal Approach to Crosslinked Hierarchical Polymer Multilayers as Stable and Highly Effective Antifouling Coatings, Advanced Materials, vol. 26, pp. 2688-2693 (2014).

Wei, Q., et al., "Multivalent anchored and crosslinked hyperbranched polyglycerol monolayers as antifouling coating for titanium oxide surfaces," Colloids and Surfaces B: Biointerfaces, vol. 122, pp. 684-692 (2014).

Banerjee, I. et al., "Antifouling coatings: recent developments in the design of surfaces that prevent fouling by proteins, bacteria, and marine organisms," Adv. Mater., vol. 23, 690-718, Feb. 8, 2011.

Barbey, R. et al., "Polymer Brushes via Surface-Initiated Controlled Radical Polymerization: Synthesis, Characterization, Properties, and Applications," Chem. Rev., vol. 109, 5437-5527, Oct. 21, 2009.

Blaszykowski, C. et al., "Surface chemistry to minimize fouling from blood-based fluids ," Chem. Soc. Rev., vol. 41, 5599-5612, Jul. 6, 2012.

Chen, D. et al., "Photopatternable Biodegradable Aliphatic Polyester with Pendent Benzophenone Groups," Biomacromolecules, vol. 16, 3329-3335, Oct. 12, 2015.

Chen, S. et al., "Polydopamine As an Efficient and Robust Platform to Functionalize Carbon Fiber for High-Performance Polymer Composites," ACS Appl. Mater. Interfaces, vol. 6, 349-356, Nov. 14, 2013.

Decher, G. "Fuzzy Nanoassemblies: Toward Layered Polymeric Multicomposites." science, vol. 277, 1232-1237, Aug. 29, 1997.

Dey, P. et al. "Hydrolytically degradable, dendritic polyglycerol sulfate based injectable hydrogels using strain promoted azide-alkyne cycloaddition reaction.", Polym.Chem., vol. 7, 375ff., Jan. 14, 2016.

Goda, T. et al., "Biomimetic phosphorylcholine polymer grafting from polydimethylsiloxane surface using photo-induced polymerization," Biomaterials, vol. 27, 5151-5160, Oct. 1, 2006.

Hong, S. et al., "Poly(norepinephrine): Ultrasmooth Material-Independent Surface Chemistry and Nanodepot for Nitric Oxide," Angewandte Chemie International Ed., vol. 52, 9187-9191, Aug. 26, 2013.

Ilharco, L.M. et al., "Infrared Approach to the Study of Adsorption on Cellulose: Influence of Cellulose Crystallinity on the Adsorption of Benzophenone," Langmuir, vol. 13, 4126-4132, Jun. 23, 1997.

Jiang, S. and Z. Cao. "Ultralow-Fouling, Functionalizable, and Hydrolyzable Zwitterionic Materials and Their Derivatives for Biological Applications." Advanced Materials, vol. 22, p. 920, Mar. 2010.

Laure, W. et al., "Switching the Wettability of Titanium Surfaces through Diels-Alder Chemistry," Chem. Mater., vol. 26, 3771-3780, Jun. 2014.

Lee, B.P. et al., "Mussel-Inspired Adhesives and Coatings," Annual review of materials research, vol. 41, 99-132, Aug. 1, 2011.

Lee, J.H. et al., "Protein-resistant surfaces prepared by PEO-containing block copolymer surfactants," J. of biomedical materials research, vol. 23, 351-368, Mar. 1989.

Liu, Y. et al., "Polydopamine and Its Derivative Materials: Synthesis and Promising Applications in Energy, Environmental, and Biomedical Fields," Chemical reviews, vol. 114, 5057-5115, Feb. 11, 2014.

Liu, X. et al., "Blood compatible materials: state of the art," J. Mater. Chem. B., vol. 2, 5718-5738, Sep. 21, 2014.

Magniez, K. et al., "Overcoming Interfacial Affinity Issues in Natural Fiber Reinforced Polylactide Biocomposites by Surface Adsorption of Amphiphilic Block Copolymers," ACS Appl. Mater. Interfaces, vol. 5, 276-283, Jan. 8, 2013.

Maier, G. et al., "Adaptive synergy between catechol and lysine promotes wet adhesion by surface salt displacement," Science, vol. 349, 628-632, Aug. 7, 2015.

Raad, I. I. et al. "The Relationship Between the Thrombotic and Infectious Complications of Central Venous catheters," J. Am. Med. Assoc., vol. 271, 1014-1016, Apr. 6, 1994.

Ryan, M et al. "Pulsed Plasma Polymerization of Maleic Anhydride." Chemistry of materials, 8, 37-42, Jan. 15, 1996.

Schuler, A.K. et al., "On the Generation of Polyether-Based Coatings through Photoinduced C,H Insertion Crosslinking," Macromol. Chem. Phys., vol. 217, 1457-1466, Mar. 7, 2016.

Wei, Q., et al., "Mussel-Inspired Dendritic Polymers as Universal Multifunctional Coatings," Angewandte Chemie International Ed., vol. 53, 11650-11655, Dec. 12, 2014.

Weinhart, M. et al., Linear Poly(methyl glycerol) and Linear Polyglycerol as Potent Protein and Cell Resistant Alternatives to Poly(ethylene glycol), Chem. Asian J. vol. 5, p. 1992, Jul. 2, 2010.

Woerz, A. et al., "Protein-resistant polymer surfaces," J. Mater. Chem., vol. 22, 19547-19561, Aug. 28, 2012.

Yu, Q. et al., "Anti-fouling bioactive surfaces," Acta Biomater., vol. 7, 1550-1557, Apr. 7, 2011.

Zhang, S., et al., "Kinetics of Polymer Interfacial Reactions: Polymer Brush Formation by Click Reactions of Alkyne End-Functional Polymers with Azide-Functional Substrates." Macromolecules, 49, 5461-5474, Jul. 27, 2016.

Zhao, B. and W. J. Brittain, "Polymer brushes: surface-immobilized macromolecules," Prog. Polym. Sci., vol. 25, 677-710, Jun. 1, 2000.

Fasting, C. et al., "Multivalency as a Chemical Organization and Action Principle," Angewandte Chemie International Ed., vol. 51, 10472-10498, Oct. 15, 2012.

Anderson, T.H., et al., "The Contribution of DOPA to Substrate-Peptide Adhesion and Internal Cohesion of Mussel-Inspired Synthetic Peptide Films," Advanced Functional Material, vol. 20, Issue, 23, pp. 4196-4205 (Dec. 8, 2010).

Arnold, M., "Activation of Integrin Function by Nanopatterned Adhesive Interfaces," ChemPhysChem, vol. 5, Issue 3, pp. 383-388 (Mar. 19, 2004).

Belegrinou, S., et al., "pH-dependent immobilization of proteins on surfaces functionalized by plasma-enhanced chemical vapor deposition of poly(acrylic acid)- and poly(ethylene oxide)-like films," Langmuir : the ACS Journal of Surfaces and Colloids, vol. 24, Issue 14, pp. 7251-7261 (Jun. 13, 2008).

Cavalcanti, W.L., et al., "Dual-purpose defenders," European Coating Journal, vol. 10, pp. 1-4 Oct. 2012.

Christensen, K., S., et al., "Gelation of copolymers with pendent benzophenone photo-cross-linkers," Macromolecules, vol. 45, Issue 12, pp. 5237-5246 (Jun. 6, 2012).

Dalsin, J.L. and Messersmith, P.B., "Bioinspired antifouling polymers," Materials Today, vol. 8, Issue 9, pp. 38-46 (Sep. 2005).

Dommerholt J. et al., "Readily accessible bicyclononynes for bioorthogonal labeling and three-dimensional Imaging of living cells," Angewandte Chemie, vol. 49, Issue 49, pp. 9422-9425 (Dec. 3, 2010).

Ejima, H., et al., "One-step assembly of coordination complexes for versatile film and particle engineering," Science, vol. 341, Issue 6142, pp. 154-157 (Jul. 12, 2013).

Esplandiu, M.J. and Noeske, P.L.M., "XPS investigations on the interactions of 1,6-hexanedithiol/Au(1 1 1) layers with metallic and ionic silver species," Applied Surface Science, vol. 199, Issue 1-4, pp. 166-182 (Oct. 30, 2002).

Firon, N., et al., "Mannose-specific adherence of Escherichia coli to BHK cells that differ in their glycosylation patterns," FEMS Microbiology Letters, vol. 27, Issue 2, pp. 161-165 (May 1985).

Fitton, A.O., et al., "Synthesis of simple oxetanes carrying reactive 2-substituents," Synthesis, Issue 12, pp. 1140-1142 (Dec. 1987).

Flemming, Hans-Curt, et al., "Biofilms: an emergent form of bacterial life," Nature Reviews, vol. 14, pp. 563-575 (Sep. 2016).

GE, J., et al., "Superparamagnetic magnetite colloidal nanocrystal clusters," Angewandte Chemie, vol. 46, Issue 23, pp. 4342-4345 (May 24, 2007).

Gervais, M., et al., "Direct Synthesis of $\alpha$-Azido,$\omega$-hydroxypolyethers by Monomer-Activated Anionic Polymerization," Macromolecules, vol. 42, Issue 7, pp. 2395-2400 (Mar. 10, 2009).

Gillich, T., "Self-Assembly of Focal Point Oligo-catechol Ethylene Glycol Dendrons on Titanium Oxide Surfaces: Adsorption Kinetics, Surface Characterization, and Nonfouling Properties," Journal of the American Chemical Society, vol. 133, Issue 28, pp. 10940-10950 (2011).

(56) References Cited

OTHER PUBLICATIONS

Gumbiner, M., B.,"Cell Adhesion: The Molecular Basis of Tissue Architecture and Morphogenesis," Cell, vol. 84, pp. 345-357 (Feb. 9, 1996).
H., H., et al., "Transition from mushroom to brush during formation of a tethered layer," ACS Publications, vol. 20, Issue 14, pp. 5770-5775 (Jul. 6, 2004).
Halan, B., et al., "Biofilms as living catalysts in continuous chemical syntheses," Trends in Biotechnology, vol. 30, Issue 9, pp. 453-465 (Sep. 2012).
Hasegawa, R., and Doi, M., "Dynamical Mean Field Calculation of Grafting Reaction of End-Functionalized Polymer," Macromolecules, vol. 30, Issue 18, pp. 5490-5493 (Aug. 15, 1997).
Hersel, U., et al., "RGD modified polymers: biomaterials for stimulated cell adhesion and beyond," Biomaterials, vol. 24, Issue 24, pp. 4385-4415 (Nov. 2003).
Hook, F., et al., "Structural changes in hemoglobin during adsorption to solid surfaces: Effects of pH, ionic strength, and ligand binding," Proceedings of the National Academy of Sciences, vol. 95, Issue 21, pp. 12271-12276 (Oct. 13, 1998).
Huang, H., and Penn, S., L., "Dense Tethered Layers by the "Grafting-To" Approach," Macromolecules, vol. 38, Issue 11, pp. 4837-4843 (May 7, 2005).
Huang, H., et al., "Effect of Segmental Adsorption on the Tethering of End-Functionalized Polymer Chains," Macromolecules, vol. 37, Issue 2, pp. 516-523 (Jan. 27, 2004).
Ishida, N. and Biggs, S., "Effect of Grafting Density on Phase Transition Behavior for Poly(N-isopropylacryamide) Brushes in Aqueous Solutions Studied by AFM and QCM-D," Macromolecules, vol. 43, Issue 17, pp. 7269-7276 (Aug. 6, 2010).
Iyer, S., K., and Luzinov, I.,"Effect of Macromolecular Anchoring Layer Thickness and Molecular Weight on Polymer Grafting," Macromolecules, vol. 37, Issue 25, pp. 9538-9545 (Nov. 13, 2004).
J., W. et al., "Reversible hemostatic properties of sulfabetaine/quaternary ammonium modified hyperbranched polyglycerol," Biomaterials, vol. 86, pp. 42-55 (Jan. 29, 2016).
Kalb, J., and Levitzki, A., "Metal-Binding Sites of Concanavalin A and their Role in the Binding of a-Methyl D-Glucopyranoside," Biochemical Journal, vol. 109, pp. 669-672 (Jun. 13, 1968).
Labbe, A. et al., "Controlled High-Speed Anionic Polymerization of Propylene Oxide Initiated by Onium Salts in the Presence of Tnisobutylaluminum," Macromolecules, vol. 40, Issue 22, pp. 7842-7847 (Oct. 3, 2007).
Lahann, J., et al., "Chemical vapour deposition polymerization of substituted [2.2]paracyclophanes," vol. 19, Issue 9, pp. 441-444 (Sep. 1998).
Lee, H., et al., "Mussel-inspired surface chemistry for multifunctional coatings.," Science, vol. 318, Issue 5849, pp. 126-430 (Oct. 19, 2007).
Ligoure, C., and Leibler, L., "Thermodynamics and kinetics of grafting end functionalized polymers to an Interface," Journal Physical France, vol. 51, pp. 1313-1328 (Jan. 1, 1990).
Lis, H., and Sharon, N., "Lectins: Carbohydrate-Specific Proteins That Mediate Cellular Recognitiont," Chemical Reviews, vol. 98, Issue 2, pp. 637-674 (Mar. 19, 1998).
Meyer, J., et al., "Poly(glycidyl amine) and Copolymers with Glycidol and Glycidyl Amine Repeating Units: Synthesis and Characterization," Macromolecules, vol. 44, Issue 11, pp. 4082-4091 (May 6, 2011).
Meyers, S.R. and Grinstaff, M.W., "Biocompatible and Bioactive Surface Modifications for Prolonged In Vivo Efficacy," Chemical Reviews, vol. 112, No. 3, pp. 1615-1632 (Oct. 18, 2011).

Qi, Z., et al., "Multivalency at Interfaces: Supramolecular Carbohydrate-Functionalized Graphene Derivatives for Bacterial Capture, Release, and Disinfection," Nano Letters, vol. 15, No. 9, pp. 6051-6057 (Sep. 9, 2015).
Ratner, D., B., "Replacing and Renewing: Synthetic Materials,Biomimetics, and Tissue Engineering inImplant Dentistry," Journal of Dental Education, vol. 65, Issue 12, pp. 1340-1347 (Dec. 2001).
Russell, P., T., "Copolymers at surfaces and interfaces," Current Opinion in Colloid & Interface Science, vol. 1, Issue 1, pp. 107-115 (Feb. 1996).
Ryu, D.Y., et al., "A generalized approach to the modification of solid surfaces," Science, vol. 308, Issue 5719, pp. 236-239 (Apr. 8, 2005).
Sakai, S., et al., "Novel chitosan derivative soluble at neutral pH and in-situ gellable via peroxidase-catalyzed enzymatic reaction," Journal of Materials Chemistry, vol. 19, Issue 2, pp. 230-235 (Apr. 22, 2009).
Siegers, C., et al., "Self-assembled monolayers of dendritic polyglycerol derivatives on gold that resist the adsorption of proteins," Chemistry, vol. 10, Issue 11, pp. 2831-2838 (Jun. 7, 2004).
Smith, D., G., et al., "Monte Carlo Simulation Study of the Kinetics of Brush Formation by Irreversible Adsorption of Telechelic Polymers onto a Solid Substrate," Langmuir, vol. 22, Issue 2, pp. 664-675 (Jan. 2006).
Sofia, J., S., et al., "Poly(ethylene oxide) Grafted to Silicon Surfaces: Grafting Density and Protein Adsorption," Macromolecules, vol. 31, Issue 15, pp. 5059-5070 (Jul. 10, 1998).
Toomey, R., et al., "Swelling Behavior of Thin, Surface-Attached Polymer Networks," Macromolecules, vol. 37, Issue 3, pp. 882-887 (Jan. 13, 2004).
Waksman, G., and Hultgren, J., S., "Structural biology of the chaperone—usher pathway of pilus biogenesi," Nature Reviews Microbiology, vol. 7, pp. 765-774 (Nov. 2009).
Wei, Q., and Haag, R., "Universal Polymer Coatings and Their Representative Biomedical Applications," Materials Horizons, vol. 2, Issue, 6, pp. 567-577 (Aug. 27, 2015).
Wei, Q., et al., "A Universal Approach to Crosslinked Hierarchical Polymer Multilayers as Stable and Highly Effective Antifouling Coatings," Advanced Materials, vol. 26, Issue 17, pp. 2688-2693 (May 7, 2014).
Wei, Q., et al., "Oxidant-induced dopamine polymerization for multifunctional coatings," Polymer Chemistry, vol. 1, Issue 9, pp. 1430-1433 (Sep. 7, 2010).
Wei, Q., et al., "Protein interactions with polymer coatings and biomaterials," Angewandte Chemie, vol. 53, Issue 31, pp. 8004-8031 (Jul. 28, 2014).
Wood, K., T., "Insights on *Escherichia coli* biofilm formation andinhibition from whole-transcriptome profiling," Environmental Microbiology, vol. 11, Issue 1, pp. 1-15 (Jan. 2, 2009).
Yu, L., et al., "Bioinspired Universal Monolayer Coatings by Combining Concepts from Blood Protein Adsorption and Mussel Adhesion," ACS Applied Materials and Interfaces, vol. 9, Issue 7, pp. 6624-6633 (Jan. 24, 2017).
Goli, K. et al., "Generation of functional coatings on hydrophobic surfaces through deposition of denatured proteins allowed by grafting from polymerization," Biomacromolecules, vol. 13, 1371-1382, 2012.
Massia, S. P. and J. A. Hubbell, "An RGD spacing of 440 nm is sufficient for integrin alpha V beta 3-mediated fibroblast spreading and 140 nm for focal contact and stress fiber formation," J. Cell Biol., vol. 114, 1089-1100, Sep. 1991.
Petrone, L. et al., "Mussel adhesion is dictated by time-regulated secretion and molecular conformation of mussel adhesive proteins," Nature Communications, 6, 8737, 12 pages, Oct. 28, 2015.

\* cited by examiner

AMPHIPHILIC BLOCK COPOLYMER AND COATING ARRANGEMENT

CROSS-REFERENCE TO A RELATED APPLICATION

This application is a National Phase Patent Application of International Patent Application Number PCT/EP2017/066313, filed on Jun. 30, 2017, which claims priority of European Patent Application Number 16177279.3, filed on Jun. 30, 2016.

BACKGROUND

The disclosure relates to an amphiphilic block copolymer and to a coating arrangement comprising such a coating compound.

Traditional surface modification technologies face many challenges due to the fast development and diversification in biomedical and chemical materials science.[1] There is increasing need for universal coating approaches that can modify a wide range of material surfaces.[2] Only a limited number of universal coating technologies have been successfully developed over the last decades.[3] However, none of them can induce the smallest possible thickness and substrate-contouring morphology of a highly controllable monolayer coating.

SUMMARY

It is an object underlying the proposed solution to provide a substance that can universally applied to build up coatings on different surfaces.

This object is addressed by an amphiphilic block copolymer having features as described herein. Such an amphiphilic block copolymer comprises a first block consisting of a polymeric hydrophilic domain, wherein the polymeric hydrophilic domain consists of a polyglycerol.

The amphiphilic block copolymer may furthermore comprise a second block consisting of a hydrophobic domain and a first linker domain, wherein the second block is covalently bound to the first block via the first linker domain. Thereby, the hydrophobic domain is chosen from the group consisting of aromatic residues having 3 to 20 carbon atoms, aliphatic residues having 3 to 20 carbon atoms, oligo(dimethylsiloxane), and poly(dimethylsiloxane).

Additionally, the amphiphilic block copolymer may comprise a third block consisting of a catechol domain and a second linker domain, wherein the third block is covalently bound to the first block via the second linker domain, wherein the catechol domain comprises at least one catechol residue.

The amphiphilic block copolymer necessarily comprises a fourth block consisting of a crosslinking domain and a third linker domain, wherein the fourth block is covalently bound to the first block via the third linker domain. Thereby, the crosslinking domain comprises a reactive residue enabling a crosslinking between individual molecules of the amphiphilic block copolymer. This reactive residue is at least one residue chosen from the group consisting of amines, thiols, allyls, vinyls, azides, alkynes, carboxyls, anhydrides, aldehydes, and benzophenone.

Thereby, the second block and the third block are only optional if the reactive residue of the fourth block is a benzophenone.

The amphiphilic block copolymer can also be denoted as coating compound. Both expressions are used interchangeably herein. Herewith disclosed is such a coating compound comprising a polymeric hydrophilic domain, a hydrophobic domain, a catechol domain, and a crosslinking domain. The hydrophobic domain is covalently bound to the hydrophilic domain via a first linker domain. Equivalently, the catechol domain is covalently bound to the hydrophilic domain by a second linker domain. Equivalently, the cross-linking domain is covalently bound to the hydrophilic domain via a third linker domain.

Thereby, the catechol domain comprises at least one catechol residue. Furthermore, the cross-linking domain comprises a reactive residue enabling a cross-linking between different molecules of the coating compound. These different molecules of the coating compound can be chemically identical or can differ in their chemical structure (as long as they comprise the domains as explained above).

Due to the presence of the catechol domain, the cross-linking domain and the hydrophobic domain, the coating compound is very well suited to be coated onto polar surfaces and non-polar surfaces. Thereby, the catechol domain allows for stable anchoring polar surfaces via coordinated and/or hydrogen bonding. The hydrophobic domain establishes a linkage on non-polar surfaces based on hydrophobic interactions. The crosslinking domain serves for stable intermolecular bonds (covalent or non-covalent or both). It must be emphasized that catechol alone is not a strict universal anchor, which only exhibits weak hydrophobic interaction on non-polar surfaces.

Thus, combining the hydrophobic domain, the crosslinking domain and the catechol domain in one and the same molecule, allows for a stable anchoring of the coating compound on different surfaces and thus a universal application of the claimed coating compound.

Thereby, the presence of the hydrophobic domain, the crosslinking domain and the catechol domain has a synergistic effect for the whole compound going far beyond a simple mixture of a first coating compound bearing a hydrophobic domain and a second coating compound bearing a catechol domain. This will be exemplarily explained in the following.

If a prior art coating compound bearing only a hydrophobic domain is applied onto a hydrophobic surface such as a polymer like polystyrene or alkylated or fluorinated surfaces, it forms only weak hydrogen bonds to the respective surface or is bonded by only weak hydrophobic interactions. Rinsing such a coating with a surfactant solution leads to a removal of the previously applied coating.

If, however, a coating compound according to the disclosure is applied to such a surface, it is possible to cross-link the individual molecules of the coating compound by oxidizing the catechol residues of the catechol domain and by achieving a crosslinking due to the crosslinking domain. Such an oxidation can be carried out with any suited oxidation agent. A coating being built up of cross-linked coating compound molecules cannot be any more simply removed from the coated surface by rinsing with a surfactant solution. Rather, it remains stably on the surface.

Thereby, it should be noted that the hydrophobic domain, the crosslinking domain and the catechol domain do not negatively influence each other upon formation of an according coating. Rather, the coating efficiency by the instantly claimed coating compounds was found to be equal to or better than the coating efficiency of coating compounds bearing only one type of anchoring group known from prior art.

If the coating compound is to be applied onto a metal, metal alloy or metal oxide surface, no oxidation of the catechol residues of the catechol domain is necessary. Rather, the catechol domain serves for stable hydrogen bonding or coordinated anchoring of the coating compound on such surfaces. Thereby, it is even more suited to avoid oxidizing conditions in order to avoid cross-linking and aggregation of the coating compound prior to contacting the surface to be coated. The crosslinking domain serves for an additional stabilization of the coating.

As indicated above, the coating compound can also be denoted as amphiphilic block copolymer. Thereby, the hydrophilic domain, the hydrophobic domain (with its linker), the catechol domain (with its linker), and the cross-linker domain (with its linker) are to be considered as individual blocks of the block copolymer.

In an embodiment, the reactive residue of the crosslinking domain is chosen from the group consisting of amines, thiols, allyls, vinyls, azides, alkynes, carboxyls, anhydrides, aldehydes, and benzophenone. Such reactive residues can be particularly easy activated to allow for cross-linking of individual coating compound molecules. An amine ($NH_2$) is a particularly suited residue for the cross-linking domain. Amines are particularly suited to build up first intermolecular connections and thus to assist in the adhesion process of the coating compound in general. An according cross-linking by amines is not as tight as a cross-linking between oxidized catechol groups but assists in the attachment of the coating compound onto a surface and in the optional subsequent tight interconnection between oxidized additional groups.

In case of an amine as functional residue of the functional domain, the coating compound can also be denoted as amphiphilic block copolymer with catecholic and amino groups in the short anchoring segment to integrate the amphiphilic interaction and catecholic anchoring, with manifold attachment and chelation as well as subsequent intralayer crosslinking to stabilize the surface coating.

In a further embodiment, the polymeric hydrophilic domain is chosen from the group consisting of polyglycerols, polyethers, polyethylene glycols, polyesters, polyamides, polyimides, polyimines, polyurethanes, polycarbonates, polyethersulfones, oligopeptides, polypeptides, and copolymers thereof. Thereby, a polyglycerol, such as a linear polyglycerol, is particularly suited to be used as polymeric hydrophilic domain. In an embodiment, an according polyglycerol comprises 10 to 1000, in particular 20 to 900, in particular 30 to 800, in particular 40 to 700, in particular 50 to 600, in particular 60 to 500, in particular 70 to 400, in particular 80 to 300, in particular 90 to 200, in particular 95 to 120, in particular 100 to 115 monomeric glycerol units. A linear polyglycerol comprising 100 to 120 glycerol units is particularly suited.

In an embodiment, the hydrophobic domain is an aromatic residue having 3 to 20 carbon atoms, an aliphatic residue having 3 to 20 carbon atoms, an oligo(dimethylsiloxane), or a poly(dimethylsiloxane). Such an aromatic residue might comprise heteroatoms such as O, N and/or S. A particularly suited residue to be used as hydrophobic domain is a substituted or non-substituted phenyl residue, in particular a non-substituted phenol residue. The hydrocarbon chain of the aliphatic residue can be interrupted by one or more oxygen, nitrogen and/or sulfur atoms. Alternatively or additionally, the hydrocarbon chain can be substituted by a group comprising one or more oxygen, nitrogen and/or sulfur atoms.

In an embodiment, any of the first, the second or the third linker domain is an alkane having 1 to 20 carbon atoms. Thereby, the hydrocarbon chain of the alkane can be interrupted by one or more oxygen, nitrogen and/or sulfur atoms. Alternatively or additionally, the hydrocarbon chain can be substituted by a group comprising one or more oxygen, nitrogen and/or sulfur atoms. To give an example, a substitution of the hydrocarbon chain by a carbonyl residue, a hydroxyl residue or by a thiol residue is possible.

It is possible to adjust the distance between the hydrophobic domain, the catechol domain and optionally the linker domain on the one hand and the polymeric hydrophilic residue on the other hand by the number of carbon atoms in the linker domains and/or by the chemical structure of the linker domains. Thereby, the coating compound can be adjusted such that it guarantees on the one hand a good attachment to polar or non-polar surfaces, but allows on the other hand a tight intermolecular interaction in form of a cross-linking between individual coating compound molecules, if such a cross-linking is desired.

In an embodiment, the first linker domain and the second linker domain are designed such that they have a similar or an identical length. This can be achieved, e.g., by using the same chemical structure for the first linker domain and the second linker domain. In doing so, the distance between the hydrophobic domain and the polymeric hydrophilic domain as well as the distance between the catechol domain and the polymeric hydrophilic domain can be set to the same value. Then, an attachment of the coating compounds to polar surfaces and non-polar surfaces can be effected in a very suited manner without any of the groups affecting the efficacy of the other group during the attachment process.

In an embodiment, the coating compound comprises 1 to 20, in particular 2 to 19, in particular 3 to 18, in particular 4 to 17, in particular 5 to 16, in particular 6 to 15, in particular 7 to 14, in particular 8 to 13, in particular 9 to 12, in particular 10 to 11 hydrophobic domains. A particularly suited amount of hydrophobic domains is 1, 2, 3, 4, 5, 6, 7, 8, 9, or 10. In addition, the coating compound comprises in this embodiment 1 to 20, in particular 2 to 19, in particular 3 to 18, in particular 4 to 17, in particular 5 to 16, in particular 6 to 15, in particular 7 to 14, in particular 8 to 13, in particular 9 to 12, in particular 10 to 11 catechol domains. A particularly suited amount of catechol domains is 3, 4, 5, 6, 7, 8, 9, or 10. It is particularly suited to provide 3 to 6 hydrophobic domains and 3 to 6 catechol domains in the coating compound. To give a further example, 5 hydrophobic domains and 5 catechol domains are well suited to be present in the coating compound The number of hydrophobic domains can generally differ from the number of catechol domains.

In an embodiment, the ratio between the number of hydrophilic monomers of the hydrophilic domain and the number of hydrophobic domains is between 10:1 and 100:1, in particular between 11:1 and 95:1, in particular between 12:1 and 90:1, in particular between 13:1 and 80:1, in particular between 14:1 and 70:1, in particular between 15:1 and 60:1, in particular between 16:1 and 50:1, in particular between 17:1 and 40:1, in particular between 18:1 and 30:1, in particular between 19:1 and 20:1.

In an embodiment, however, the number of hydrophobic domains equals the number of catechol domains.

In a further embodiment, the number of cross-linking domains is equal to or lower than the number of hydrophobic domains and/or the number of catechol domains. A suited number of cross-linking domains is 1 to 20, in particular 2 to 19, in particular 3 to 18, in particular 4 to 17, in particular 5 to 16, in particular 6 to 15, in particular 7 to 14, in particular 8 to 13, in particular 9 to 12, in particular 10 to 11. A particularly suited amount of cross-linking domains is 1, 2, 3, 4, 5, 6, 7, 8, 9, or 10.

In an embodiment, the coating compound comprises 100 to 120 glycerol units making up the hydrophilic domain, 5 to 15 hydrophobic domains, 5 to 15 catechol domains and 2 to 10 crosslinking domains.

In an embodiment, the coating compound comprises a functional domain covalently bound to the hydrophilic domain. The functional domain can be bound directly or via a fourth linker domain to the hydrophilic domain. Thereby, the functional domain comprises a functional group that facilitates chemical reactions of the hydrophilic domain. A suited functional group is an azide group or a halogen, such as a fluoride residue, a chloride residue, a bromide residue or an iodide residue. A bromide residue is particularly suited to be used as functional residue of the functional domain. The functional domain enables a particular simple post modification of the whole coating compound so that a substrate coated by the coating compound can be subjected to subsequent chemical reactions.

In an embodiment, the coating compound comprises a sugar residue, such as a mannitol residue, covalently bound to the hydrophilic domain (first block). It can be easily introduced into the amphiphilic block copolymer by making use of a functional domain, e.g. an azide group.

In an aspect, the disclosure relates to an amphiphilic block copolymer that only comprises the first block (i.e., the polymeric hydrophilic domain in the nature of a polyglycerol) and the fourth block, but no second and no third blocker. The reactive residue of the fourth block is then a benzophenone. The inventors surprisingly found that stable anchoring of the amphiphilic block copolymer on the surface can already be established if benzophenone is used as reactive residue being part of the fourth block. Benzophenone does not only crosslink individual molecules of the block copolymer, but also builds up chemical bonds to a surface on which the block copolymer is to be anchored.

Therefore, in an embodiment, benzophenone is chosen as reactive residue for the fourth block.

In another embodiment, the amphiphilic block copolymer comprises the first block, the second block, the third block and the fourth block. Thus, in this embodiment, the second block and the third block are non-optional. Then, the individual blocks can particularly well exhibit the synergistic effects discussed above.

In an embodiment, the third block is present if the second block is present. In an embodiment, the second block is present if the third block is present.

The disclosure also relates to coating arrangements comprising a substrate and an amphiphilic block copolymer or a coating compound, respectively, according to the previous explanations. Thereby, the coating compound is bonded onto the surface of the substrate.

In an embodiment, the coating compound is bonded to the surface such that it builds up exclusively a monolayer on the surface of the substrate. This facilitates the formation of an equally distributed coating on the substrate and reduces the risk of an unwanted premature dissolution of the coating from the substrate surface.

As explained above, this bonding is likely to occur by a coordinated and/or hydrogen bonding in case of polar surfaces (such as metal, metal alloy or metal oxide surfaces) or by hydrophobic interactions in case of non-polar surfaces. A covalent bonding between the coating compound and the substrate is also possible.

In an embodiment, different types of bonds are established between the coating compound and the surface of the substrate. Thus, it is possible that the coating compound is bonded to the substrate by hydrophobic interactions, by hydrogen bonds, by coordinated bonds and/or by covalent bonds at the same time.

In an embodiment, the substrate comprises at least one material chosen from the group consisting of metals, metal alloys, metal oxides, glass, silica, graphene, and polymers. In an embodiment, the substrate fully consists of one or more of these materials. Particularly suited metals are aluminum, silver, copper and gold. A particularly suited metal alloy is steel. Particularly suited metal oxides are titania ($TiO_2$), aluminum oxide and zinc oxide. A particularly suited graphene is thermally reduced graphene oxide (TRGO). Particularly suited polymers are synthetic polymers such as polydimethylsiloxane (PDMS), polystyrene (PS), polypropylene (PP), poly(methyl methacrylate) (PMMA), polytetrafluoroethylene (PTFE), and polyvinyl chloride (PVC).

It is also possible to apply the coating compound onto an already existing coating of the base material of the substrate. In an embodiment, the substrate is already coated by a hydrophobic coating substance. Such a hydrophobic coating substance can comprise an alkane and/or a halogen in to provide an alkylated or a halogenated substrate material. A particularly suited form of halogenation is a fluorination. Thus, the coating compounds can be applied onto an already existing fluorinated surface, such as a PTFE surface.

Herewith disclosed is also a stepwise dip-coating process to achieve universal monolayer coatings with a few nanometers thickness on macro-scale and nano-scale surfaces or interfaces.

All previously discussed embodiments can be combined in any desired way. Thereby, it is possible to apply embodiments described with respect to the claimed coating compound to the described coating arrangement or the described method, and vice versa.

BRIEF DESCRIPTION OF THE DRAWINGS

Aspects of the proposed solution will be explained in more detail making reference to exemplary embodiments and the enclosed figures.

DETAILED DESCRIPTION

Figure 1:
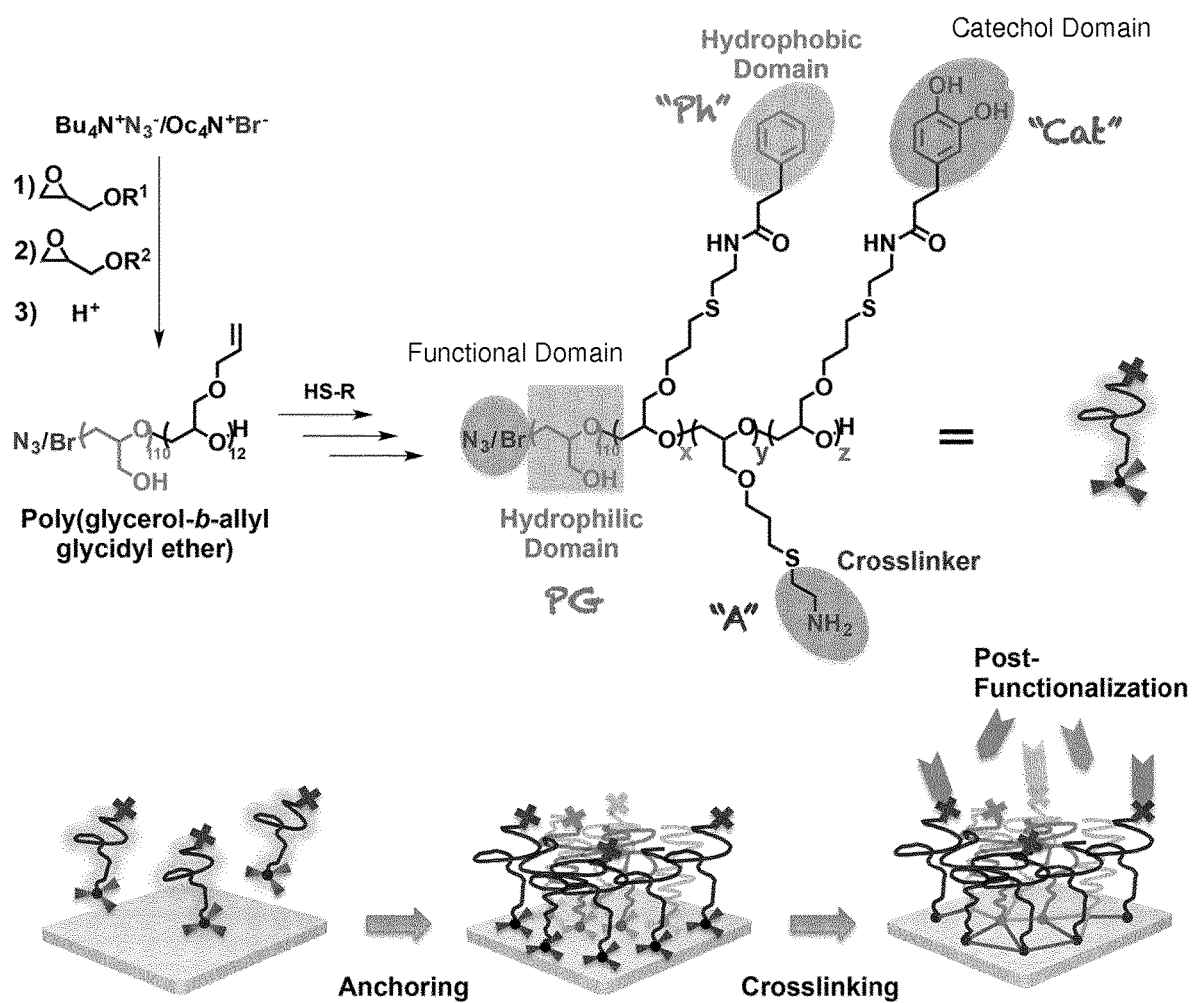
FIG. 1 is a schematic depiction of a manufacturing process of PG-CatPh as an embodiment of the coating compound as well as of an exemplary application of PG-CatPh.

FIG. 1 is a schematic depiction of a manufacturing process of PG-CatPh as an embodiment of the coating compound as well as of an exemplary application of PG-CatPh. The polyglycerol (PG)-based block copolymer ($M_n$=9000 g·$mol^{-1}$, polydispersity=1.2) with a polyglycerol block (about 110 repeat units) and a poly(allyl glycidyl ether) block (statistically 12 repeat units) was synthesized by ring-opening anionic polymerization. The polyglycerol block serves as a hydrophilic domain that prevents adsorption of excess polymers to maintain the monolayer coatings. The poly(allyl glycidyl ether) block can be functionalized with an amine residue (2 units) as crosslinking domain, a catechol residue (5 units) as catechol domain, and a phenyl residue (5 units) as hydrophobic domain by thiol-ene chemistry. The resulting molecule is referred to as PG-CatPh. The crosslinking domain, the catechol domain and the hydrophobic domain serve together as anchor domain.

The catechol groups allow polymers to be stably anchored on polar surfaces via coordinative and/or hydrogen bonding, [4] while the hydrophobic domains, i.e., phenyl groups, initiate adsorption on non-polar surfaces to form monolayers as the first step. The oxidation of catechols, which induces crosslinking and aggregation,[5] should be avoided in this step by using acidic conditions. UV-vis spectra of PG-CatPh at pH 6 in MOPS buffer and under oxidative conditions revealed that catechol groups can be kept stable in a buffer at pH 6, but is rapidly oxidized under oxidative conditions. Specifically, an increased absorption at 350 nm representing quinone formation and an increased absorption at 279 and 450 nm indicate the crosslinking between quinone and catechol groups. Photos of PG-CatPh solutions showed that the color of PG-CatPh solution in oxidative conditions changed from colorless to yellow in 20 min, but the color of PG-CatPh solution in acidic conditions still kept colorless even after 24 h.

Overall, the three types of groups in the anchor domain (hydrophobic domain, catechol domain and crosslinking domain) synergistically contribute to surface anchoring. Besides the main function of the groups described above, catechol and amine groups also donate hydrogen bonding, electrostatic attraction, and coordinative interaction. Phenyl groups prevent a facile autoxidation of catechols and provide additional hydrophobic interactions. Moreover, due to the self-limiting mono-layer adhesion, the amphiphilic block copolymer PG-CatPh is also suitable for the coating of nanosystems, e.g., sheets and particles.

In order to identify the effects of the hydrophobic domain, the catechol domain, and the crosslinking domain on the surface attachment, quartz crystal microbalance (QCM) with dissipation was employed to analyze the adsorption of the polymers on the substrates selected in a way to cover a wide range of distinct hydrophilic or hydrophobic terminal groups.

Dynamic online coating results show that about 800-1000 ng/cm$^2$ block copolymer PG-CatPh adsorbed on different types of sensor surfaces, including gold (Au), titania (TiO$_2$), silica (SiO$_2$), polystyrene (PS), as well as alkylated and fluorinated self-assembled monolayers on Au sensors. The results are shown in FIGS. 2a to 2f.

Figure 2:
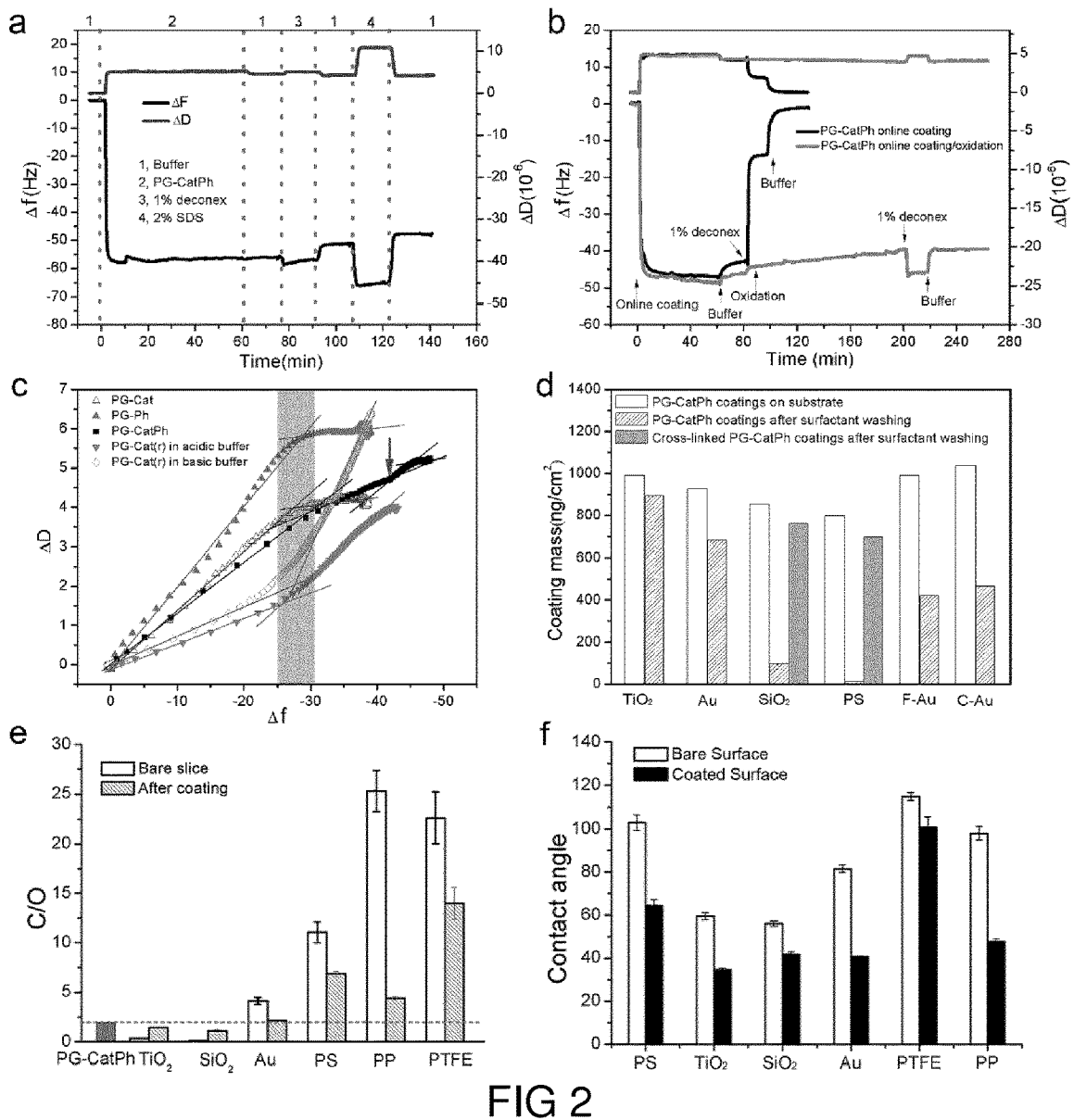
FIG. 2a shows the QCM frequency and dissipation shift as a function of time during the adsorption of the block copolymer PG-CatPh on $TiO_2$.
FIG. 2b shows the QCM frequency and dissipation shift as a function of time during the adsorption of the block copolymer PG-CatPh on PS.
FIG. 2c shows ΔD-Δf plots of the adsorption of PG-Cat, PG-Ph, PG-CatPh, and PG-Cat(r) on PS sensor surfaces.
FIG. 2d shows the amount of the adsorbed block copolymer PG-CatPh on different types of sensor surfaces.
FIG. 2e shows the [C]/[O] concentration ratio of the different surfaces before and after being coated with PG-CatPh block copolymers.
FIG. 2f shows the average static water contact angle of different bare and coated surfaces.
Figure 3:
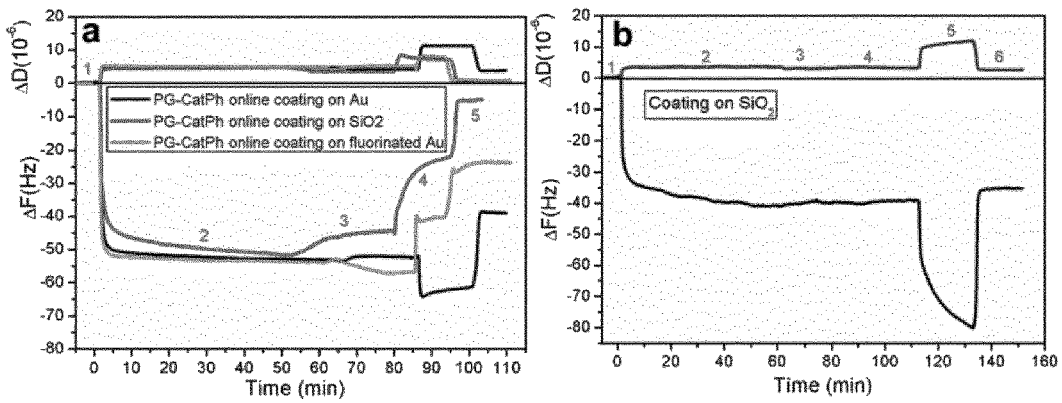
FIG. 3a shows the QCM frequency and dissipation shift as a function of time during the adsorption of the block copolymer PG-CatPh on Au, $SiO_2$, and fluorinated sensor surfaces.
FIG. 3b shows an online coating and crosslinking curve of PG-CatPh on $SiO_2$ surface.

Under acidic condition, catecholic polymers can only anchor on metal oxide surfaces as monolayer coatings.[6] The amount of the adsorbed PG-CatPh on all the tested surfaces was similar to the amount found on TiO$_2$ surfaces, which indicates the formation of monolayer coatings on these surfaces. However, the copolymers on SiO$_2$, PS, alkylated, and fluorinated surfaces, which were only tethered by weak hydrogen bonding or hydrophobic interaction, could be easily rinsed away by surfactant solutions (cf. FIG. 3). Therefore, these coatings were crosslinked by oxidization of the catechol groups. The obtained crosslinked coatings maintained stable under rinsing with surfactant solutions (FIG. 2d). The stability is comparable with the coatings on metal or metal oxide surfaces. Unless otherwise specified, the PG-CatPh coatings in the following part were not crosslinked on metal/metal oxide surfaces but crosslinked on all other surfaces.

Figure 4:
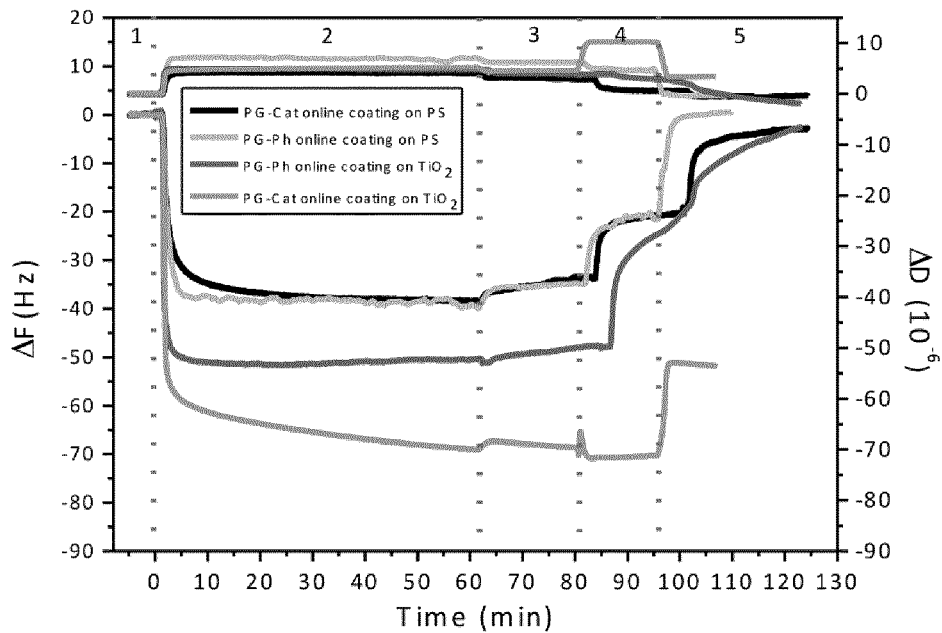
FIG. 4 shows the QCM frequency and dissipation shift as a function of time during the adsorption of the block copolymer PG-Ph on $TiO_2$, PG-Ph on PS, PG-Cat on $TiO_2$, and PG-Cat on PS.

For comparison, the amino-functionalized poly(glycerol-b-allyl glycidyl ether) (PG-A) without any catechol or phenyl groups could not be adsorbed in significant amounts on the tested surfaces. PG-Ph without catechol groups was found to adsorb on both TiO$_2$ and PS surfaces like blood proteins would do, but it was as easily removed by surfactant solutions as non-crosslinked PG-CatPh on PS surfaces (FIG. 4). As expected, PG-Cat was stably immobilized on TiO$_2$ surfaces and also adsorbed on PS surfaces via hydrophobic interactions. However, the catechol groups are more polar than phenyl groups, which resulted in a less efficient adsorption of PG-Cat compared to PG-CatPh on PS surfaces (FIG. 4).

Furthermore, the viscoelastic properties of the polymer coatings were investigated by evaluating ΔD (dissipation shift) vs. Δf (QCM frequency shift) graphs during the adsorption processes (FIG. 2c). In case of both PG-Cat and PG-Ph during adsorption, the ΔD vs. Δf plots displayed two phases with significantly different slopes. The slope of the second phase ($|\partial D/\partial f_2{}_{PG\text{-}Cat}|$=0.02, $|\partial D/\partial f_2{}_{PG\text{-}Ph}|$=0.012) was obviously smaller than that of the first phase ($|\partial D/\partial f_1{}_{PG\text{-}Cat}|$=0.147, $|\partial D/\partial f_1{}_{PG\text{-}Ph}|$=0.205). This indicates that loosely bound coatings formed in the first phase.[7] In the second phase, ΔD only slightly increased with the increasing |Δf|, i.e., the adsorbed polymers in this phase did not cause any further increase in the amount of trapped water in coatings.[8] Therefore, the adsorbed polymers in this phase filled into the space of the very flexible coatings that formed in the first phase and produced dense coatings.

In contrast, the adsorption of catecholic random copolymer PG-Cat(r), which had similar structure to most of the presented catecholic polymers, also displayed two phases on PS surfaces. However, the slope in the second phase is larger than that of the first phase under both acidic and oxidative conditions, which is caused by the stacking of the random polymer chains and the formation of the crosslinked multilayer coatings.[9] The graphs of the adsorption of PG-CatPh show two periods (before and after the arrow) and four phases (FIG. 2c and FIG. 6), which is attributed to the combined effects of the catechol and phenyl induced adsorption. The slopes in both periods decreased in the second phase, and the slope in the final phase was close to 0. Therefore, the adsorption profile matches the adsorption mechanism of PG-Cat and PG-Ph. A detailed discussion of the ΔD-Δf plots of the adsorption will be given in the following.

Figure 5:
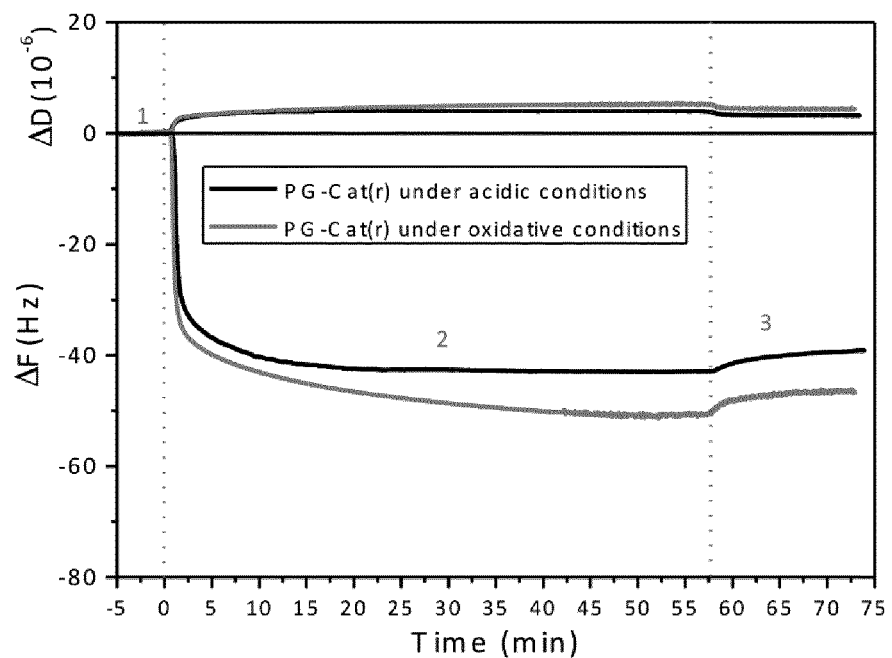
FIG. 5 shows the QCM frequency and dissipation shift as a function of time during the adsorption of random copolymer PG-Cat(r) under acidic and oxidative conditions on PS sensor surfaces.

The adsorption of PG-Cat, PG-Ph, PG-CatPh, and PG-Cat(r) under acidic conditions achieved equilibrium on PS surfaces during the 60 min experimental time (FIG. 2b, FIG. 4, and FIG. 5). However, in the case of PG-Cat(r) under oxidative conditions, the adsorption equilibrium could not be achieved in a comparable time frame.

To simplify the adsorption models, the adsorption of PG-Cat and PG-Ph on PS surfaces was first analyzed. The frequency (f) response of QCM include the contributions from polymer adsorbates and water molecules that were bound to the polymer chains of the coatings.[17] Energy dissipation (D) changes represent the rigidity of the coatings, which is related to the hydration ratio and the conformations of the adsorbed polymers.[7,8] As explained above, the ΔD vs. Δf plots displayed two phases with significantly different slopes in case of both PG-Cat and PG-Ph during adsorption. The polymer chains were very flexible and accompanied by a larger amount of surrounding water.

Some more details are that the block copolymers loosely adsorbed on the surfaces in the first phase and achieved saturated flexible coatings at the break point of the D-f plots. The corresponding Δf at the break points for both PG-Cat and PG-Ph plots was about −27 Hz. Therefore about 478 ng/cm$^2$ polymers were adsorbed as saturated flexible coatings after 8.22 min for PG-Cat and 7.63 min for PG-Ph, respectively. In the following period, about 213 ng/cm$^2$ polymers were still adsorbed on the substrates and caused the rearrangement of the polymer chains to develop the final dense coatings (about 691 ng/cm$^2$ polymers).

The adsorption of catecholic random copolymer PG-Cat(r) on PS surfaces under acidic and oxidative conditions was investigated as well. The graphs also display two phases. Under acidic conditions, the slope after the break point ($|\partial D/\partial f_2\ _{PG\text{-}Cat(r)}|$=0.1524) is about 2.4 times larger than before ($|\partial D/\partial f_1\ _{PG\text{-}Cat(r)}|$=0.064), whereas the slope increased to a 4.5 times higher value under oxidative conditions ($|\partial D/\partial f_2\ _{PG\text{-}Cat(r)O}|$=0.356, $|\partial D/\partial f_1\ _{PG\text{-}Cat(r)O}|$=0.080). The stacking of the random polymer chains must have caused the slightly increased slope in the former case. In the latter case, the oxidized catechol groups resulted in crosslinking and multilayer formation[9], which led to the significant increase of D.[7]

The break points of the PG-Cat(r) plots are similar to the PG-Cat and PG-Ph plots (about −27 Hz), which indicate the similarity of the saturated and flexible coatings for the different copolymers. The slope of the first phase of PG-Cat (r) plots is smaller than that of PG-Cat and PG-Ph plots, because the random copolymers with multiple anchoring sites randomly distributed in the polymer chains mostly laid flat on the substrates. In comparison, the block copolymers with all anchor groups in the short block segment preferably stood up on the substrates. In the second phase, random copolymers without oxidized catechols exhibited chain stacking rather than chain rearrangement, and random copolymers with oxidized catechols formed multilayer coatings. Only defined block copolymers exhibited a chain rearrangement that formed highly dense monolayer coatings.

Figure 6:
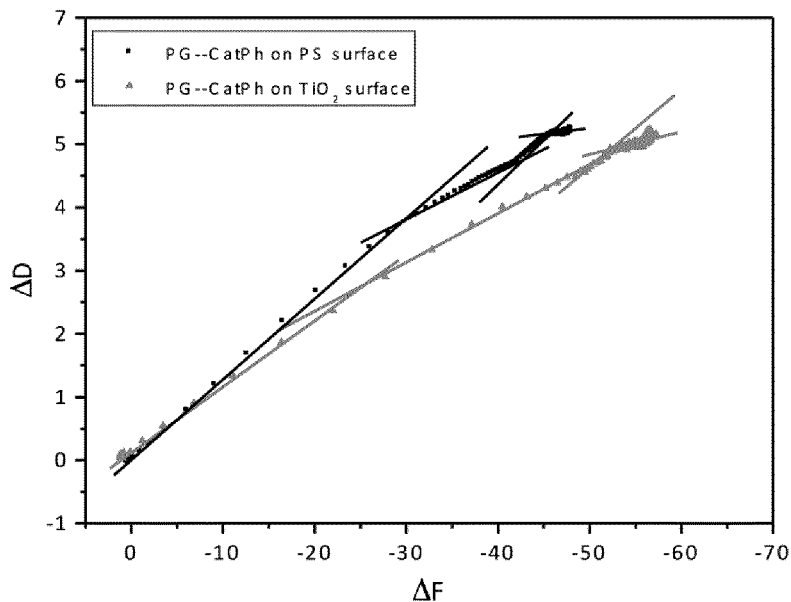
FIG. 6 shows plots on dissipation shift over QCM frequency of the adsorption of PG-CatPh on PS and $TiO_2$ sensor surfaces.

The graphs of the adsorption of PG-CatPh show two periods (before and after the arrow in FIG. 2c) and four phases, which is attributed to the combined effects of the catechol and phenyl induced adsorption. The slopes in both periods decreased in the second phase, and the slope in the final phase was close to 0. Therefore, the adsorption profile matches the adsorption mechanism of PG-Cat and PG-Ph and the discussion above. Compared to the PG-Cat and PG-Ph plots, the PG-CatPh plot showed a smaller average slope and larger final |Δf|. Hence, the bifunctional anchors tethered the polymers more stable than single catechol or phenyl anchors. Moreover, the adsorption of PG-CatPh on $TiO_2$ surface had a similar profile to the adsorption on PS surfaces (FIG. 6). The only difference is that the average slope of the adsorption on $TiO_2$ was a little smaller than on PS, which may be due to the even more stable coordinative bonding on $TiO_2$ surfaces.

The chemical composition of selected PG-CatPh coatings on planar substrates was confirmed by X-ray photoelectron spectroscopy (XPS) analysis. The C, N, O, and S compositions of all of the coated surfaces [Au, $TiO_2$, $SiO_2$, PS, polypropylene (PP), and polytetrafluoroethene (PTFE)] approached the values of the PG-CatPh polymers (FIG. 2e and Table 1).

TABLE 1

XPS elemental surface composition of the bare and PG-CatPh coated surfaces.

| Samples | Ti % | Si % | Au % | F % | C % | N % | O % | S % |
|---|---|---|---|---|---|---|---|---|
| PG-CatPh | — | — | — | — | 64.2 | 1.38 | 33.05 | 1.38 |
| Bare $TiO_2$ | 26.27 | — | — | — | 16.08 | — | 52.47 | — |
| Coated $TiO_2$ | 7.62 | — | — | — | 52.12 | 1.45 | 38.03 | 1.05 |
| Bare $SiO_2$ | — | 32.33 | — | — | 5.48 | 0.11 | 61.62 | — |
| Coated $SiO_2$ | — | 14.52 | — | — | 45.79 | 1.24 | 37.37 | 1.02 |
| Bare Au | — | — | 68.09 | — | 25.7 | 0.41 | 4.86 | — |
| Coated Au | — | — | 15.53 | — | 56.38 | 1.04 | 26.51 | 0.53 |
| Bare PTFE | — | — | — | 65.81 | 32.79 | — | 1.05 | — |
| Coated PTFE | — | — | — | 60.85 | 35.65 | 0.19 | 2.9 | 0.08 |
| Bare PP | — | — | — | — | 96.81 | — | 2.94 | — |
| Coated PP | — | — | — | — | 78.83 | 1.1 | 18.83 | 0.68 |
| Bare PS | — | — | — | — | 91.08 | 0.79 | 7.44 | — |
| Coated PS | — | — | — | — | 84.56 | 1.39 | 12.56 | 0.56 |

Figure 7:
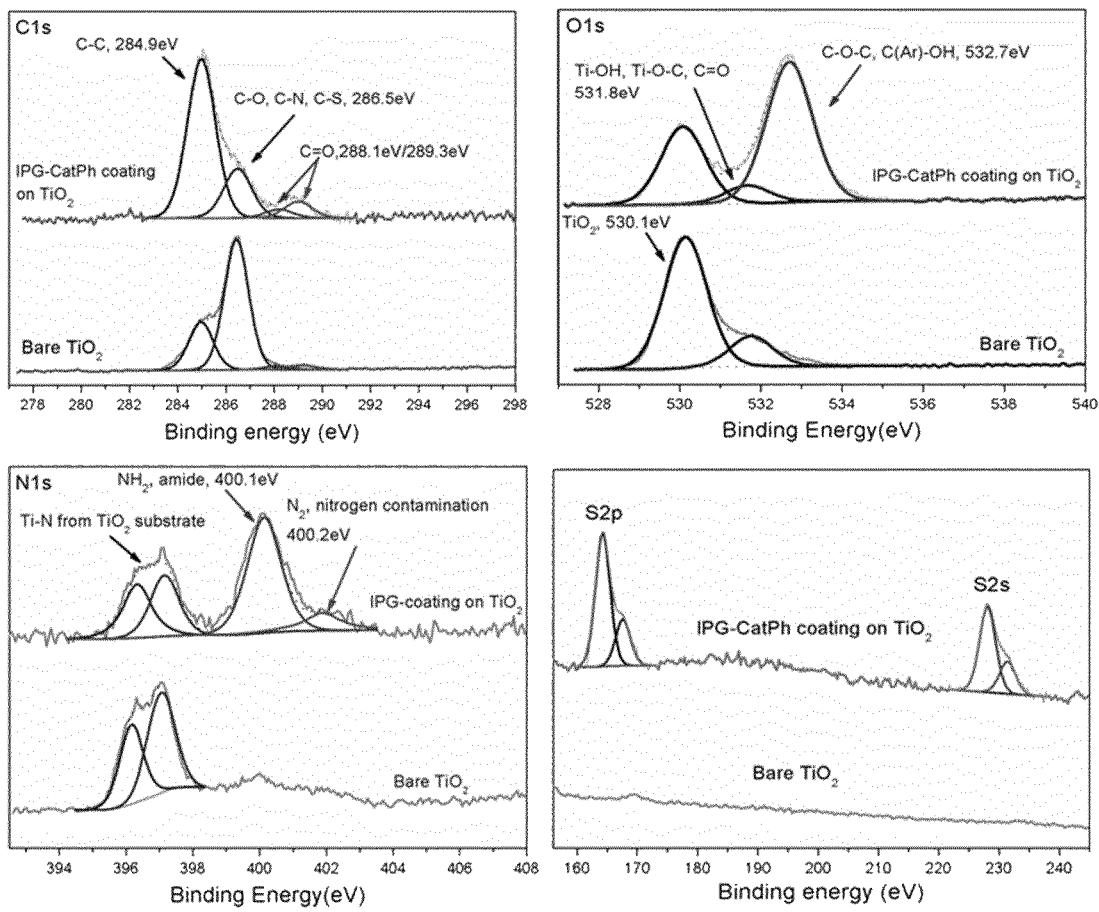
FIG. 7 shows deconvoluted C1s, N1s, O1s and S2s, S2p signal curves of PG-CatPh coating on $TiO_2$ substrate and the corresponding bare $TiO_2$ substrate.

According to the deconvoluted C1s signals (Table 2, FIG. 7), the signal attributed to C—O bonds (286.5 eV, $C_B$), which are rich in PG-CatPh polymers, dramatically increased on the tested surfaces ($TiO_2$, $SiO_2$, and PS) after coating. The coatings on $TiO_2$ surfaces were analyzed in more detail. The concentration of carbon atoms in C*—O bonds (286.5 eV, $C_B$, 52.1%×70.3%) divided by the signal of oxygen next to aliphatic or aromatic carbons (O*—C, 533.0 eV, $O_C$, 38.0%×65.8%) was 1.46, which was very close to 1.5, the theoretical value of the PG backbone. The uniform and dramatic changes of the signals after coating indicate that the composition of the PG-CatPh coatings is independent of the substrate.

TABLE S2

XPS deconvoluted C1s and O1s signals of the bare and PG-CatPh coated surfaces.

| | $C_{1s}$ | | | | $O_{1s}$ | | |
|---|---|---|---|---|---|---|---|
| Samples | $C_A$ % | $C_B$ % | $C_C$ % | $C_D$ % | $O_A$ % | $O_B$ % | $O_C$ % |
| Bare $TiO_2$ | 66.3 | 22.6 | 3.8 | 7.4 | 80.9 | 17.2 | 1.9 |
| Coated $TiO_2$ | 25.6 | 70.3 | 2.0 | 2.1 | 28.4 | 5.9 | 65.8 |
| Bare PS | 90.1 | 5.9 | 0.5 | 2.5 | — | — | 100 |
| Coated PS | 74.8 | 22.1 | 0.7 | 0.8 | — | — | 100 |
| Bare SiO2 | 68.5 | 21.1 | 3.9 | 6.5 | — | — | 100 |
| Coated SiO2 | 32.4 | 63.2 | 2.2 | 2.2 | — | — | 100 |

$C_A$: C—H, C—C, C=C (284.9 eV);
$C_B$: C—O, C—N (286.5 eV);
$C_C$: C=O (288.1 eV)
$C_D$: O=C—O (289.3 eV)
$O_A$: Oxidic oxygen of the $TiO_2$ substrate (530.1 eV); $O_B$: oxygen in Ti—OH, Ti—O—C, and the carbonyl oxygen, C=O* (531.8 eV); $O_C$: oxygen next to aliphatic or aromatic carbon, C—O*H, C—O*—C (532.7 eV) or in $SiO_2$ substrate.

Figure 8:
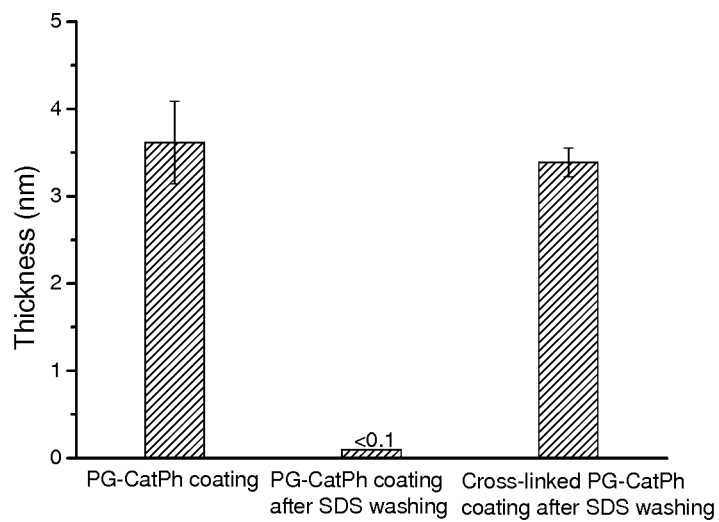
FIG. 8 shows the thickness of PG-CatPh coatings on $SiO_2$ surfaces measured by ellipsometry.

The obtained thickness of the coatings on Au, $TiO_2$, and $SiO_2$ surfaces that was calculated by the attenuation of the characteristic signals of the substrates was about 3.1±0.1, 3.1±0.1, and 2.8±0.3 nm, respectively. These results of measurements in high vacuum were slightly smaller than the results of the thickness measurement in ambient conditions by ellipsometry on $SiO_2$ wafers, which is about 3.6±0.5 nm. The ellipsometry measurement further confirmed the stability of the crosslinked PG-CatPh coatings during washing with surfactant solutions (FIG. 8).

The thickness in ambient conditions was also measured by atomic force microscopy (AFM). The values were 4.5±1.1, and 4.6±0.7 nm for the coatings on $TiO_2$ and PS surfaces, respectively. More importantly, the surface morphology of the substrates that was investigated by AFM dramatically changed after being coated by PG-CatPh. The island-like structures could be clearly observed on the coatings and had the typical morphology of a monolayer polymer brush coating.[10] The grafting density of the polymer chains was about 312±50 and 250±40 per $\mu m^2$ on $TiO_2$ and PS surfaces, respectively.

Figure 9:
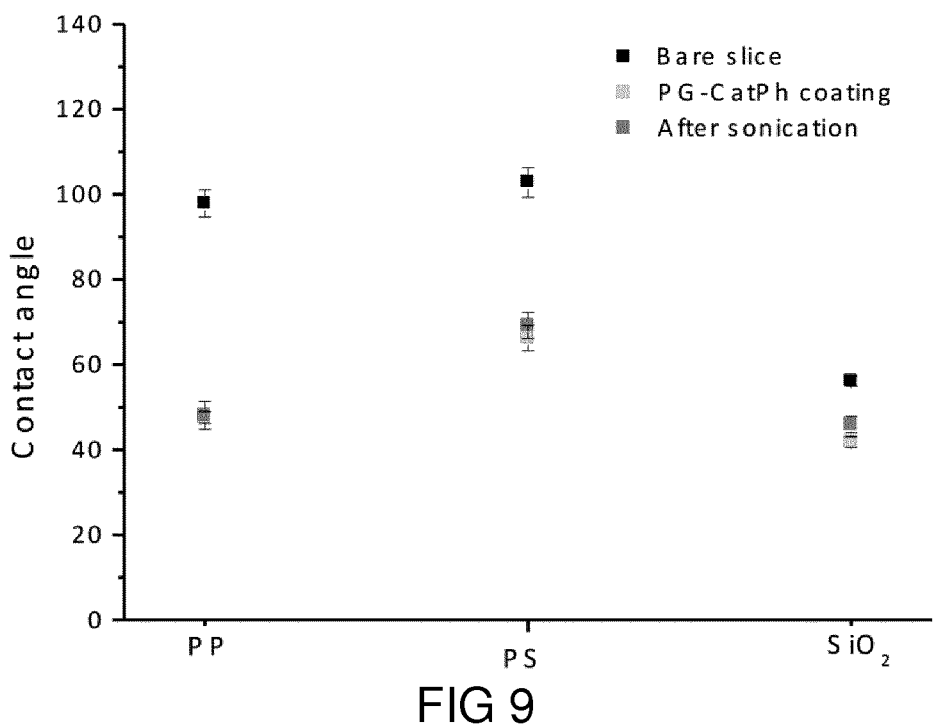
FIG. 9 shows the average static water contact angle of the coated surfaces before and after treatment by sonification for 10 min.

The monolayer coatings were very smooth. Both the average roughness (Ra) and root-mean-square roughness (Rq) of the coatings were slightly smaller than those of the bare substrates, i.e., coatings filling the grooves of the substrates. It is worthwhile to mention here that the coatings were colorless due to their small height and smoothness. The PG-CatPh coatings also changed the original wetting property of the substrates (FIG. 2f). The static water contact angles of the coatings did not obviously increase after the slides were incubated in PBS buffer or in a SDS solution (2%, w/w) for 60 days, even under sonication (FIG. 9). In addition, the coatings were slightly dissolved at pH 2 buffer but kept stable at pH 12 buffer. These tests demonstrated the high stability of the coatings under physiological conditions.

Figure 11:
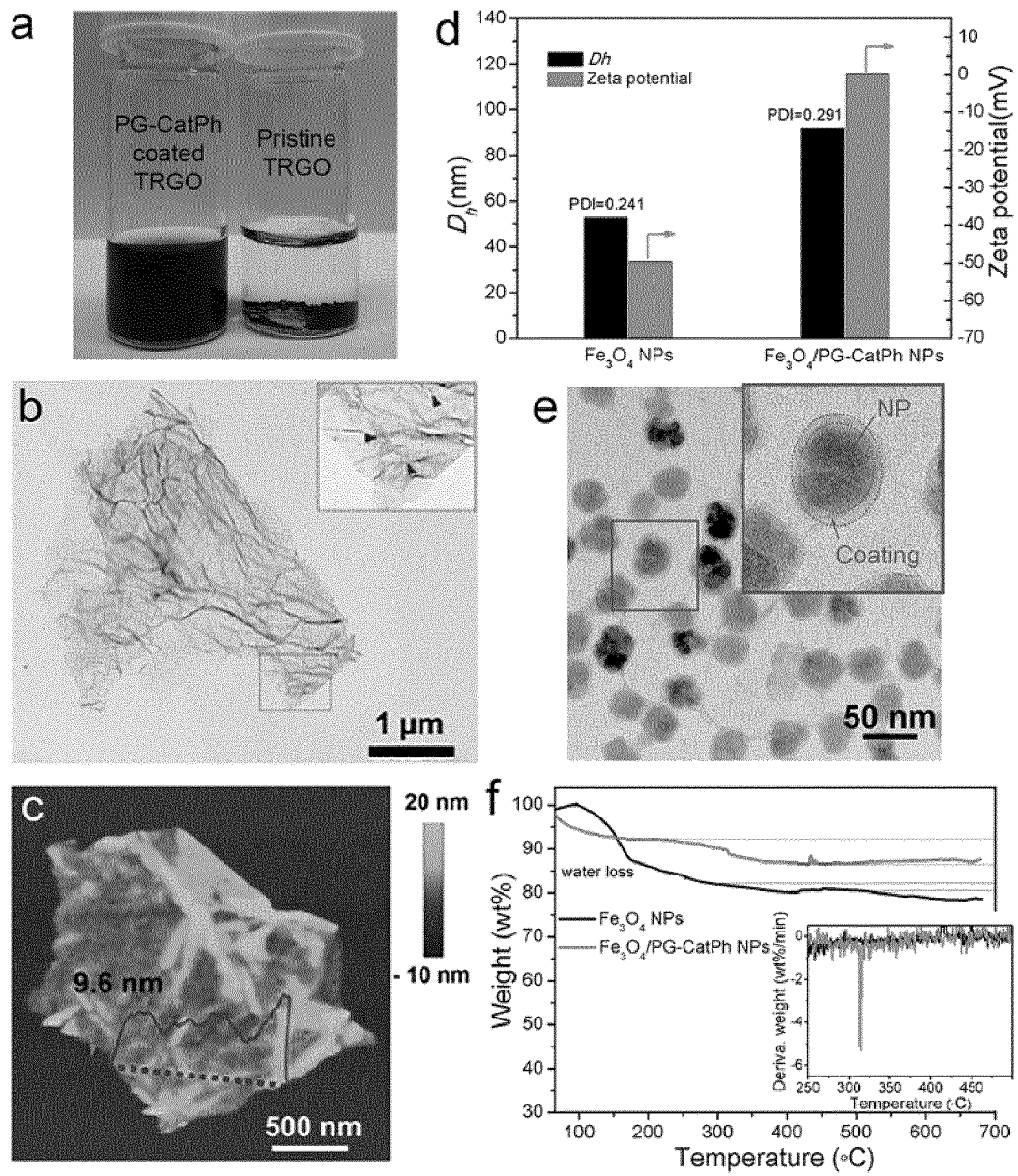
FIG. 11a shows a photograph obtained 12 hours after preparing aqueous dispersions of PG-CatPh-TRGO (left) and TRGO (right) nano-systems.
FIG. 11b shows typical TEM images of PG-CatPh-TRGO nanosheet.
FIG. 11c shows AFM height images of PG-CatPh-TRGO.
FIG. 11d shows the change of diameter and zeta potential of $Fe_3O_4$ nanoparticles after PG-CatPh coating.
FIG. 11e shows a TEM image of PG-CatPh coated $Fe_3O_4$ nanoparticles.
FIG. 11f shows TGA curves of $Fe_3O_4$ and PG-CatPh coated $Fe_3O_4$ nanoparticles.

Besides the composition of the substrates, PG-CatPh coatings are also independent of size, shape, and structure of the materials. Thermal reduced graphene oxide (TRGO) sheets were rapidly coated and dispersed under ultra-sonication in the solution of PG-CatPh for 5 min (FIG. 11a). Transmission electron microscopy (TEM) and AFM images (FIGS. 11b and 11c) confirmed the polymer coatings and indicated the thickness was similar to the height results obtained from the monolayer coating on planar substrates. PG-CatPh also obviously altered the diameter and zeta potential of the $Fe_3O_4$ nanoparticles but not the poly-dispersity index (PDI) (FIG. 11d). The polymer coatings were further confirmed by TEM (FIG. 11e) as well as the thermogravimetric analysis (TGA) and the derivative thermogravimetric (DTG) curve (FIG. 11f). The monolayer polymer coatings on nanosystems will be discussed in the following in more detail.

To examine whether this block copolymer can also form a robust coating on other dimensional material surfaces, the two most representative nanomaterials were chosen for the coating experiments, namely thermal reduced graphene oxide (TRGO) expected to provide strong surface hydrophobic interaction and $Fe_3O_4$ nanoparticles (stabilized by polyacrylic acid) with both hydrophobic interaction and catecholic anchoring.

To obtain PG-CatPh coated TRGO (PG-CatPh-TRGO), TRGO and PG-CatPh were firstly transferred into 2 mL pH 6 MOPS buffer, and then the coating was rapidly finished under ultra-sonication for 5 min to obtain the PG-CatPh-TRGO. As shown in FIG. 11a, the pristine TRGO exhibited poor water dispersibility and precipitated within 2 min even after 30 min sonication. However, the PG-CatPh-TRGO showed much higher stability due to the strong interactions between the attached hydrophilic polymer chains and water molecules, which facilitated maintaining stable dispersion in deionized water for more than one week. The individual nanosheets dispersion of PG-CatPh-TRGO was demonstrated by transmission electron microscope (TEM) and AFM measurements. Nanosheet aggregation was not observed.

In the TEM image (FIG. 11b) PG-CatPh-TRGO displays a typical wrinkle-like characteristic structure of 2D graphene sheet. However, the low electron-transparent and abundant polymer protuberances indicate that PG-CatPh polymers have been successfully coated onto the TRGO surface. For the AFM images shown in FIG. 11c, TRGO nanosheets were evenly coated with a layer of PG-CatPh. As a result, the thickness of PG-CatPh-TRGO increased to 9.6 nm from 0.7 nm of pristine TRGO. A high-resolution AFM image showed that the TRGO sheet is uniformly and continuously decorated with PG-CatPh polymer brushes. The thickness of the two-side coated PG-CatPh-TRGO sheets ranged from 7.4 nm to 11.0 nm and the average thickness of PG-CatPh-TRGO was calculated to be 9.2 nm. Therefore, the average height of the PG-CatPh coatings was 8.5 nm, which indicates that the thickness of polymer coating for each side was 4.25 nm. This result is similar to the height results obtained from the monolayer coating on $TiO_2$ and PS substrates. Therefore, it can be concluded that the PG-CatPh polymers form only single-layer coatings on TRGO.

Figure 10:
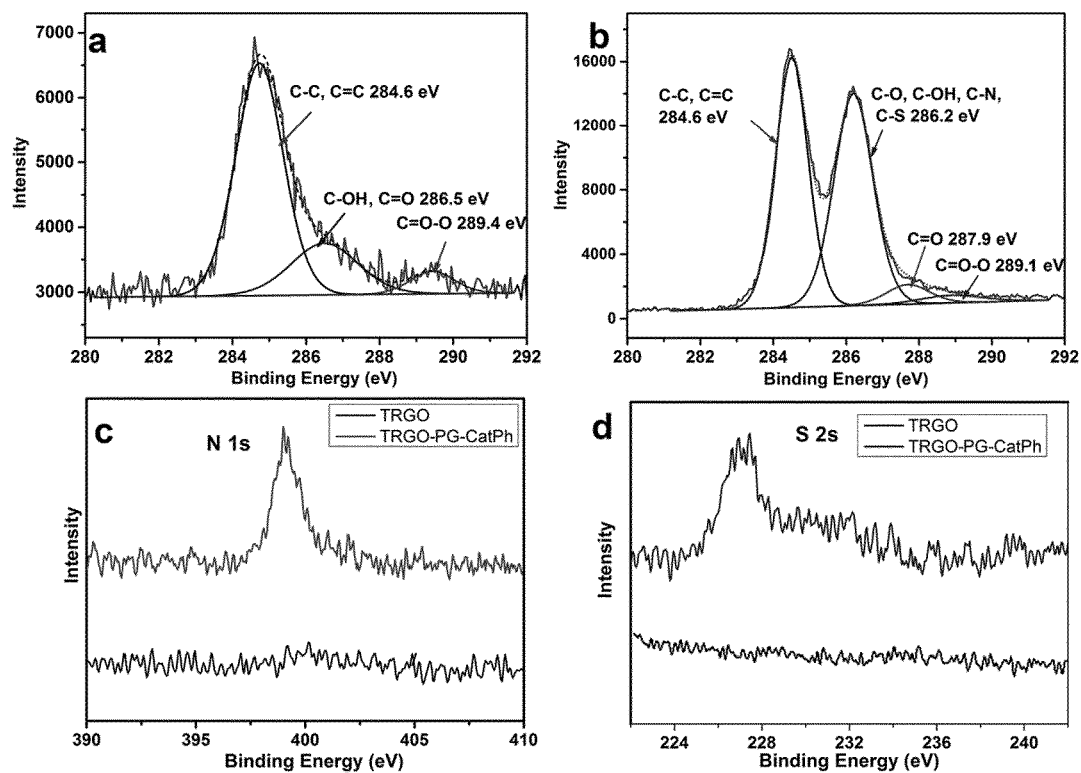
FIG. 10a shows an XPS C1s spectrum for TRGO.
FIG. 10b shows an XPS C1s spectrum for PG-CatPh-TRGO.
FIG. 10c shows N1s spectra for TRGO and PG-CatPh-TRGO.
FIG. 10d shows S2s spectra for TRGO and PG-CatPh-TRGO.

XPS was employed to further evaluate and confirm the successful achievement of PG-CatPh coatings on TRGO (FIG. 10). To sum up, the PG-CatPh polymers have been uniformly and robustly coated on TRGO surfaces. The exposed hydrophilic moieties of the coatings hinder the formation of agglomerates, and therefore the findings demonstrate the universal coating ability of polymers from macro-scale planar surfaces to nano-interfaces.

$Fe_3O_4$ nanoparticles (NPs) stabilized by poly (acrylic acid) were also coated by PG-CatPh. The diameter increased from 52 nm (included poly (acrylic acid) layer) to 92 nm after coating without obvious increase of polydispersion index (PDI) (FIG. 11d). The zeta potential of the coated $Fe_3O_4$ NPs changed from −50 mV to about 0 mV, which indicates that the NPs were fully covered by neutral polyglycerol brushes. After coating with PG-CatPh, the $Fe_3O_4$ NPs were able to disperse in water, forming a clear solution and keeping stable in dispersion state even after one month, whereas the non-coated NPs precipitated after only one week. The TEM image of the coated $Fe_3O_4$ NPs (FIG. 11e) shows a homogeneous coating layer with average thickness about 3.5 nm. This thickness was comparable to the dry thickness on macro-scale planar substrates and nano-graphene sheets. Therefore, the PG-CatPh coating onto $Fe_3O_4$ NPs can be considered as monolayer coating as well.

A thermogravimetric analysis (TGA) was applied to further characterize the coatings (FIG. 11f). The dramatic weight loss of around 20% observed for the non-coated NPs between 100 and 300° C. was ascribed to the evaporation of water molecules that physically and/or chemically adsorbed onto the high (specific) surface area of the NPs. The weight loss between 300 and 700° C. was only less than 2%. For comparison, the TGA curve of the coated NPs showed that the mass only slightly decreased between 100 and 300° C., because the adsorbed water molecules were evicted by PG-CatPh polymers. The decomposition peak around 320° C. can be identified from the derivative thermogravimetric (DTG) curve, which was corresponding to the decomposition of polyglycerol (PG) moieties[18]. The weight loss was about 6.3% when the temperature increased from 300° C. to 700° C. These results unambiguously demonstrated that the PG-CatPh effectively coated onto the $Fe_3O_4$ NPs, and a dense monolayer coating was formed surrounding the NPs surface.

Figure 12:
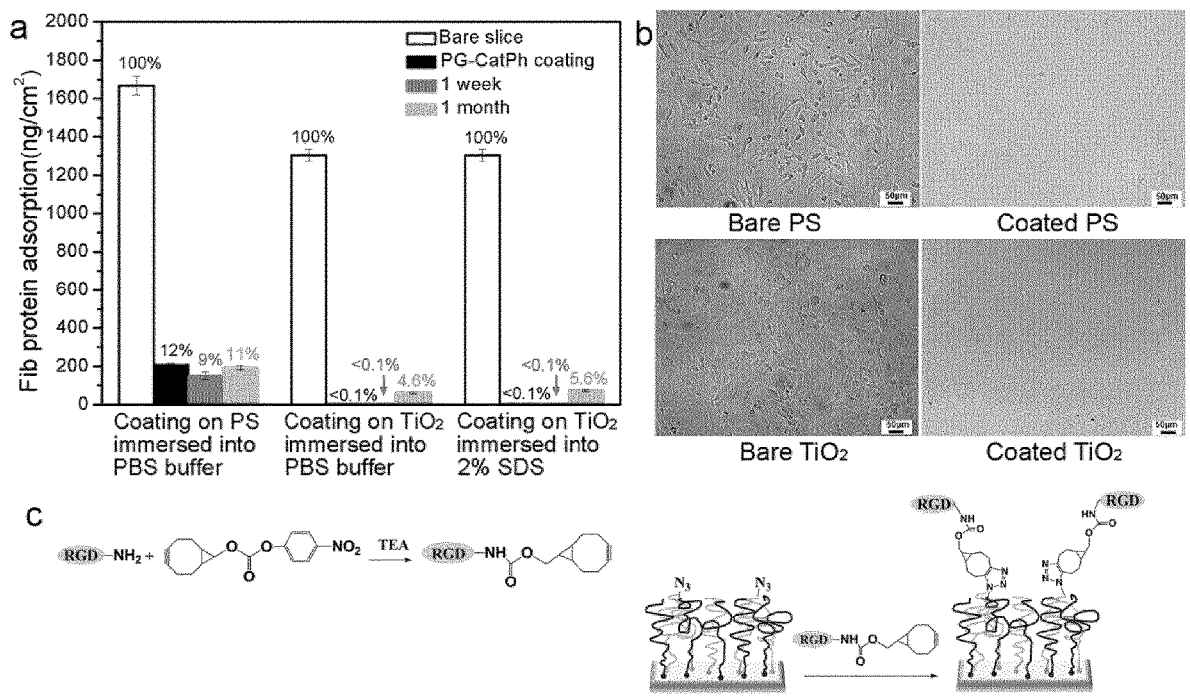
FIG. 12a shows the desorbed amount of fibrinogen (Fib) on PG-CatPh coated $TiO_2$ and PS surfaces.
FIG. 12b shows NIH3T3 cell adhesion on PG-CatPh coated $TiO_2$ and PS surfaces.
FIG. 12c shows a scheme of post-functionalization with RGD peptide by azide-alkyne cycloaddition to PG-CatPh coatings.

Both PG-CatPh coated $TiO_2$ and PS efficiently prevented the adsorption of fibrinogen (Fib) and the adhesion of NIH3T3 mouse fibroblasts (FIGS. 12a and 12b) due to the bioinert and long polyglycerol block of the polymers. After immersing the coatings in PBS buffer or SDS solution (2%, w/w) for one week (third columns in each case), the adsorbed amount of Fib was almost unchanged. The amount only slightly increased after immersing for one month (FIG. 12a; fourth columns in each case). This proved again the high stability of the coatings in physiological conditions and/or even in surfactant aqueous solutions.

While the coatings prevent unspecific biological interactions, the polymer chains were chemically active for secondary functionalization and selective interaction. For example, the cyclic RGDfK [c(RGDfK)] peptide, which primarily binds to αvβ3 integrin of cells[11], was covalently grafted onto the PG-CatPh coatings with azide terminal groups on PTFE substrates via strain-promoted azide-alkyne cycloaddition.[12] As a result, a large number of MC3T3 osteoblasts spread on the modified surfaces after one day (FIG. 11c). The well constituted paxillin clusters as the focal adhesions and the formation of the organized actin stress fibers in the cells on the c(RGDfK) immobilized surfaces indicated stable integrin-mediated cell adhesion.

Discussion of the Antifouling Performance of the Monolayer Coatings

The hydration ratio of the PG-CatPh coatings exposed to an aqueous environment can be estimated from the hydration mass and the ambient thickness, which reached about 50% and 30% on $TiO_2$ and PS surfaces, respectively. Single-protein adsorption and cell culture experiments proved that these highly hydrated bioinert polymer coatings may be applied as antifouling surfaces.[19] Both PG-CatPh coated $TiO_2$ and PS showed better resistance against the adsorption of fibrinogen (Fib) than the unmodified surfaces (FIG. 12a).

Only <0.1% Fib was adsorbed on the coated $TiO_2$ relative to the bare surfaces, while, about 12% Fib was adsorbed on the coated PS relative to the bare surfaces. Cellular adhesion studies were performed with NIH3T3 mouse fibroblasts (FIG. 12b). Cells grew to confluence on the bare surfaces after only 3 days, whereas, only a few unspread cells stayed on the coated surfaces (without rinsing the surfaces). Based on these properties, the antifouling performance of the present coatings was even better than our previously reported polyglycerol based hierarchical multilayer coatings.[9]

Discussion of the Secondary Functionalization of the Coatings to Promote Cell Adhesion For [c(RGDfK)] peptide modification, the azide terminated PG-CatPh polymers (10%) were mixed with the bromide terminated PG-CatPh polymers (90%) to control the grafting density of the c(RGDfK). The resulting grafting density is far more than the critical minimum density for stable cell spreading. As reported previously [20], the critical distance of the integrin ligands that limited cell spreading is approximately 70 nm, i.e., 0.7 fmol/cm².

After culturing MC3T3 osteoblasts for one day, a large number of cells had been attached to the c(RGDfK) immobilized surfaces with a regularly spreading, while only a few cells could be observed on bare and PG-CatPh coated surfaces without c(RGDfK) functionalization (FIG. 12c). The molecular formation of focal contacts and the assembly of actin stress fibers in the cells were investigated by immunostaining for paxillin and filamentous actin. Well constituted paxillin clusters could be clearly observed as the focal adhesions and the formation of the organized actin stress fibers in the cells on the c(RGDfK) immobilized surfaces, which indicates stable integrin-mediated cell adhesion. In contrast, non-organized paxillin and actin localization are observed by blurred molecular distribution imaging in cells that adhered on the surfaces without c(RGDfK)s.

Synthesis of Poly (ethoxyethyl glycidyl ether)-Block-Poly (allyl glycidyl ether) (PEEGE-b-PAGE)

Figure 13:
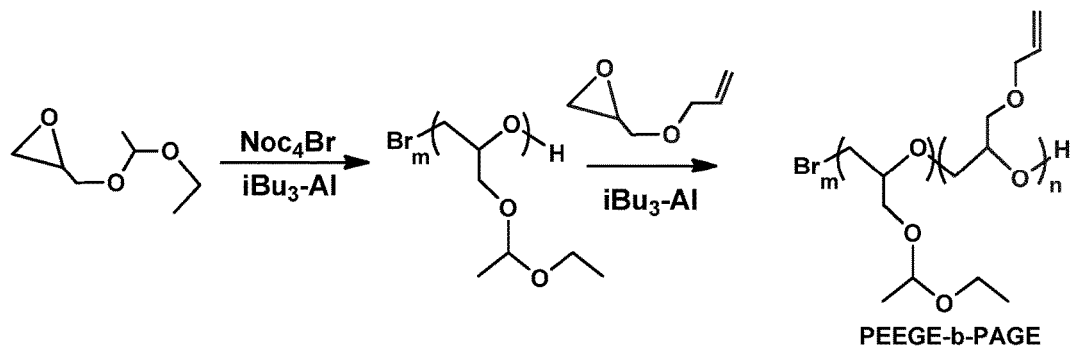
FIG. 13 shows the chemical reaction scheme of the synthesis of Poly(ethoxyethyl glycidyl ether)-block-Poly(allyl glycidyl ether) (PEEGE-b-PAGE).

This block copolymer was synthesized by the anionic copolymerization of EEGE and AGE monomers according to the scheme depicted in FIG. 13. Firstly, Tetraoctylammonium bromide (546 mg, 1 mmol) was heated to melting temperature under vacuum to remove the trace water. After cooling down to room temperature, 140 mL abs. toluene was added into the Schlenk flask under argon to dissolve this initiator. Then 19.3 mL EEGE (137 mmol) were added into the solution. The polymerization was started by adding the triisobutylaluminium (1.8 mL, 2 mmol) at a constant temperature of 0° C. 3 hours later, AGE (1.48 g, 13 mmol) and triisobutylaluminium (1.8 mL, 2 mmol) were added into the mixture while cooling with an ice bath. The reaction mixture was allowed to warm up to room temperature and stirred overnight. After polymerization, 1 mL water was added to stop the reaction and then the mixture was dried with $Na_2SO_4$. A colorless polymer was obtained after removal of toluene under reduced pressure. Then the product was dissolved into $Et_2O$ and centrifuged to remove the residues of initiator and catalyst. The product was further purified by dialysis in dichloromethane and a kind of honey-like compound was got with a yield of 94%.

$^1$H-NMR (400 MHz, $CDCl_3$, $TMS_{int}$): Repeating units δ=1.1-1.18 (—$CH_2$—$CH_3$, 3H), 1.21-1.28 (CH—$CH_3$, 3H), 3.35-4.05 (polymer backbone: $CH_2$—CH($CH_2$O)O, $CH_2CH_3$, O—$CH_2$—CH=$CH_2$), 4.6-4.8 (OCH($CH_3$)O, 1H), 5.07-5.26 ($CH_2$=CH—, 2H), 5.75-5.95 ($CH_2$=CH—, 1H).

$M_{n,GPC,THF}$=18486, $Mw/M_n$=1.179

The ratio of EEGE/AGE was calculated from $^1$H-nuclear magnetic resonance ($^1$H-NMR) spectra. The molecular weight before and after de-protection was measured by gel permeation chromatography (GPC). The calculated repeating units of the block copolymer was: $PEEGE_{110}$-b-$PAGE_{12}$.

De-Protection of PEEGE-b-PAGE

Figure 14:
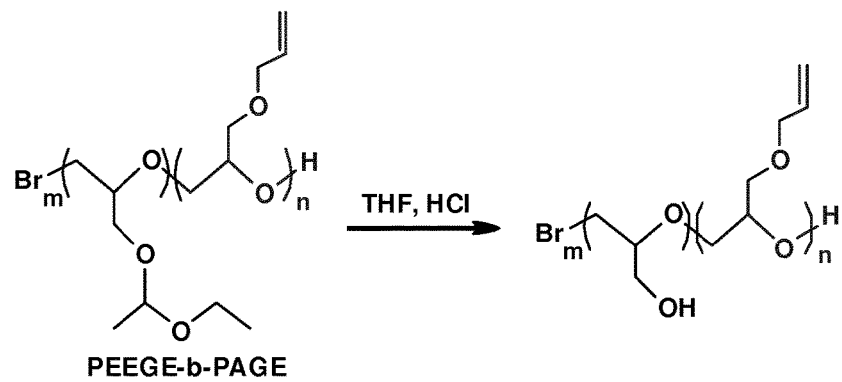
FIG. 14 shows the chemical reaction scheme of the de-protection of PEEGE-b-PAGE.

The acetal-protected PEEGE block would afford a polyglycerol block with —OH as the side groups after being de-protected under acidic conditions according to the reaction scheme indicated in FIG. 14. A general procedure of the de-protection was like this: PEEGE-b-PAGE (3 g) was dissolved into THF (100 mL) and an appropriate amount of hydrochloric acid aqueous solution (37%) was added. The precipitation appeared immediately under acidic condition. The mixture was stirred for 10 hours at room temperature. Subsequently, the supernatant was decanted, and the polymer was washed with THF, and then further purified by dialysis in methanol. The desired PG-b-PAGE was obtained as colorless viscous oil (92%) after drying in high vacuum.

$^1$H-NMR (400 MHz, Methanol-$d_4$, $TMS_{int}$): Repeating units δ=3.4-4.1 (polymer backbone: $CH_2$—CH($CH_2$O)O, O—$CH_2$—CH=$CH_2$), 5.05-5.35 ($CH_2$=CH—, 2H), 5.8-6.0 ($CH_2$=CH—, 1H).

$M_{n,GPC,H2O}$=9039, $Mw/M_n$=1.21

Thiol-Ene Reaction (PG-A)

The thiol-ene reactions were carried out by UV irradiation (~1.2 mW/cm², λ=365 nm) under ambient laboratory conditions. As a general procedure, an amount of PG-b-PAGE and cysteamine hydrochloride (4 eqv. to allyl groups) was dissolved into methanol. Then 2,2-dimethoxy-2-phenylacetophenone (Irgacure 651, 2% eqv. to allyl groups) was added and the reaction was conducted under the irradiation of 365 nm UV light at room temperature. The reaction was monitored via $^1$H-NMR and completed in 3 hours. The product was purified by dialysis in methanol.

$^1$H-NMR (400 MHz, Methanol-$d_4$, $TMS_{int}$): Repeating units δ=1.78-1.92 (O—$CH_2$—$CH_2$—$CH_2$—S, 2H), 2.60-2.71 (O—$CH_2$—$CH_2$—$CH_2$—S, 2H), 2.77-2.86 (S—$CH_2$—$CH_2$—N, 2H), 3.11-3.18 (S—$CH_2$—$CH_2$—N, 2H), 3.43-3.86 (PG backbone).

Synthesis of PG-b-P (AmGE-g-catechol/phenyl) (PG-CatPh)

Figure 15:
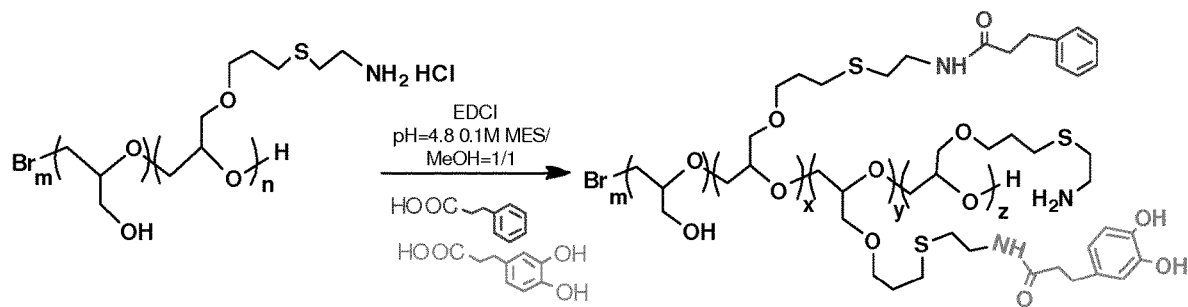
FIG. 15 shows the chemical reaction scheme of the synthesis of PG-b-P (AmGE-g-catechol/phenyl) catechol/phenyl) (PG-CatPh).

The catechol and phenyl functionalized linear polyglycerol was prepared by the coupling reaction between amino groups of PAGE block and the carboxyl groups of 3,4-dihydroxyhydrocinnamic acid (DHHA) and phenylpropionic acid according to the scheme depicted in FIG. 15. The grafting density of catechol groups and phenyl groups was precisely controlled by the equivalence ratio of amino groups to carboxyl groups in morpholinoethanesulfonic acid (MES) buffer according to a literature.[21]

The poly(glycerol)-b-poly(amino glycidyl ether) (PG-b-PAmGE) and 1-Ethyl-3-(3-dimethylaminopropyl) carbodiimide hydrochloride (EDCI, 6 eqv. to amino groups) were dissolved into pH 6 MES aqueous buffer/Methanol (1/1, v/v) mixture solvent. Then 3,4-dihdroxyhydrocinnamic acid (3 eqv. to amino groups) and phenylpropionic acid (3 eqv. to amino groups) were added into the mixture and gently stirred overnight at room temperature. The product was purified by dialysis and the grafting density of catechol groups and phenyl groups was calculated by the $^1$H-NMR.

$^1$H-NMR (400 MHz, Methanol-$d_4$, TMS$_{int}$): Repeating units δ=1.78-1.92 (O—CH$_2$—CH$_2$—CH$_2$—S, 2H), 2.30-3.20 (O—CH$_2$—CH$_2$—CH$_2$—S, S—CH$_2$—CH$_2$—N, 2H, S—CH$_2$—CH$_2$—N, 2H, CO—CH$_2$—CH$_2$—Ar), 3.43-4.12 (PG backbone), 6.45-7.0 (Ar—H, 3H from catechol group), 7.1-7.5 (Ar—H, 5H from phenyl group).

The polymers that were only functionalized with catechol groups or phenyl groups were synthesized in a similar procedure.

TABLE 3

The generated copolymers with different amount of catechol groups, phenyl groups, and amino groups were listed in the table with corresponding abbreviation:

| Polymer | Abbreviation | Hydroxyl | Catechol | Phenyl | Amine |
|---|---|---|---|---|---|
| PG$_{110}$-b-P(Cat$_{10}$-A$_2$) | PG-Cat | 110 | 10 | — | 2 |
| PG$_{110}$-b-P(Ph$_{10}$-A$_2$) | PG-Ph | 110 | — | 10 | 2 |
| PG$_{110}$-b-P(Cat$_5$-Ph$_5$-A$_2$) | PG-CatPh | 110 | 5 | 5 | 2 |
| PG$_{110}$-b-PA$_{12}$ | PG-A | 110 | — | — | 12 |
| PG$_{110}$-r-P(Cat$_5$-Ph$_5$-A$_2$)* | PG-CatPh(r) | 110 | 5 | 5 | 2 |

*The random copolymer PG$_{110}$-r-(Cat$_5$-Ph$_5$-A$_2$) was prepared in a similar procedure of PG$_{110}$-b-P(Cat$_5$-Ph$_5$-A$_2$). (b: block copolymer, r: random copolymer)

Figure 16:
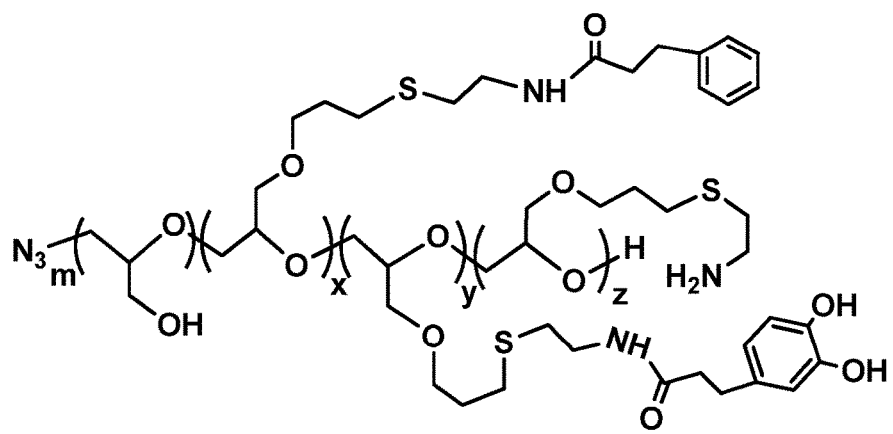
FIG. 16 shows the chemical structure of PG-b-P (AmGE-g-catechol/phenyl) (PG-CatPh) with azide as functional terminal group.

Synthesis of PG-b-P (AmGE-g-catechol/phenyl) (PG-CatPh) with Azide as the Terminal Groups The PG-CatPh polymers with α-azido groups (their chemical structure is depicted in FIG. 16) were prepared in a similar strategy like PG-CatPh with α-Br group above. The prior PEEGE-b-PAGE block copolymers with α-azido groups were synthesized from ring-opening anionic polymerization with the azido-initiator tetrabutylammonium azide (NBu$_4$N$_3$) according to a literature.[22] The polymer molecular weight and the repeating unit of EEGE and AGE in this copolymer were designed the same as the PEEGE-b-PAGE with α-Br group above.

As an alternative, after deprotection reaction, the PG-b-PAGE block copolymers with α-Br group could also react with NaN$_3$ in DMF to convert the α-Br group into α-azido group.[23] Then the catechol groups and phenyl groups were immobilized to polymer chains via thiol-ene reaction and amide coupling, respectively.

Immobilization of Cyclic RGDfK [c(RGDfK)] on PG-CatPh Coatings

α-azido terminated PG-CatPh and α-Br terminated PG-CatPh (1/9, w/w) were coated onto PTFE substrates using dip-coating method with the pH 6 MOPS buffer as the solution. The coating was further cross-linked by K$_2$S$_2$O$_8$ in pH 8.6 MOPS buffer. The coated PTFE slides were subsequently immersed into dimethylformamide (DMF). Then the bicyclo[6.1.0]non-4-yn-9-ylmethyl(4-nitrophenyl)carbonate (BCN) modified c(RGDfk) (1 mM) was added. The c(RGDfk) would grafted onto coating surface via catalyst free azide-alkyne cycloaddition reaction between N$_3$ groups from the coating surface and cyclooctyne groups from RGD-BCN. After 48 hours of reaction at room temperature, the functionalized slides were washed with methanol and water, and then dried with N$_2$ stream.

The realization of the experiments explained above will be described in the following in even more detail.

Coating on Planar Surfaces

TiO$_2$ was cleaned ultrasonically in water and methanol firstly, and then treated with UV-Ozone for 20 min before using. Polystyrene (PS), Polytetrafluoroethylene (PTFE) and polypropylene (PP) were only cleaned ultrasonically in water and methanol. The SiO$_2$ was cleaned by freshly prepared piranha solution (H$_2$SO$_4$/H$_2$O$_2$=3:1) for 30 min, followed by successive rinsing with Milli-Q water and methanol. Gold slides were also cleaned by piranha solution but for 30 s. All the QCM slices were cleaned according to the standard cleaning protocol from LOT-Quantum Design GmbH, Darmstadt, Germany.

To prepare monolayer PG coatings, pH 6 MOPS buffer was used. In the acidic condition, the catechol groups in the block polymer were kept in catechol state instead of quinone state to prevent the multilayer formation that caused by the crosslinking and self-polymerization of catechol/quinone groups. The cleaned slides were immersed in the solution of 1 mg/mL PGs at pH 6 MOPS buffer at room temperature for 2 h. It must be emphasized that the concentration of the polymer solutions for coating is always 1 mg/ml, which is far smaller than the critical micelle concentrations of the polymers (>30 mg/ml). After that, the slides were thoroughly rinsed with Milli-Q water and methanol and then dry by N$_2$ stream. The protocol of online coating by using QCM has been described in QCM part. For non-metal substrate, the interaction between catechol and substrate surface was not strong enough. The crosslinking treatment was conducted by using oxidant in basic buffers. The coated slides were immersed into 1 mg/mL K$_2$S$_2$O$_8$ in pH 8.6 MOPS buffer solution for 1 h to trigger the crosslinking and self-polymerization of catechol/quinone groups.

Coating on Nanosheet-Interfaces and Nanoparticle-Interfaces

To make the coating on thermal reduced graphene oxide (TRGO), TRGO[14] (1 mg) and PG-CatPh (5 mg) were firstly transferred into a small flask and then 2 mL pH 6 MOPS buffer was added. The coating was rapidly finished under sonication for 10 min and the coated TRGO was further washing with Milli-Q water by centrifugation at least 4 times to remove the free PG-CatPh. The centrifuged PG-CatPh coated TRGO can be easily re-dispersed in water just with hand shaking; the oven-dried PG-CatPh-TRGO can be re-dispersed by sonication.

The PG-CatPh coating on Fe$_3$O$_4$ nanoparticles (Poly (acrylic acid), $M_n$=1800 Da, was used as the stabilizer, prepared according to the method reported by J. P. Ge, et. al. [15]) was conducted in a similar method as TRGO.

UV-Vis

The reactivity and stability of IPG-Cat in acidic solution (pH=6 MOPS buffer) and basic solution (pH=8.6 MOPS buffer+1 mg/mL K$_2$S$_2$O$_8$) were measured at room temperature using UV-vis spectroscopy at wavelengths from 200 to 1100 nm.

Thermogravimetric Analysis (TGA)

Thermogravimetric analysis was performed on a Linseis STA PT 1600 thermogravimetric analyzer using the Linseis Data Acquisition software with a temperature range from room temperature to 800° C. and a rate of 10° C./min. Aluminium oxide crucibles (0.12 mL) were heated once to 800° C. before measuring the zero curve with empty crucible. Data was analyzed using Linseis Evaluation software.

Water Contact Angle

Static contact angle measurements were performed by using a contact angle goniometer (DataPhysics Instruments, Germany) with the sessile drop method. A liquid drop of 2 µL Milli-Q water was placed on the substrate and allowed to equilibrate for 15 s at room temperature. At least eight measurements were averaged to get a reliable value.

Atomic Force Microscopy (AFM)

The AFM results were recorded by a MultiMode Nanoscope V scanning probe microscopy (SPM) system (Bruker, USA) in the air under ambient conditions. The commercially available AFM cantilever tips with a force constant of ~48 N/m and resonance vibration frequency of ~330 kHz were used, and the scanning rate was set at 0.8 Hz. The AFM samples for PG-CatPh-TRGO were prepared by dropping aqueous dispersion of PG-CatPh-TRGO (~0.01 mg/mL, sonicated for 5 minutes with an ultrasonic bath cleaner) on freshly cleaved mica surface and dried under vacuum at 60° C. The AFM mode, Peak Force QNM, was used in order to better control the force with which the tip interacts with the surface. PPP-NCLR-20 probes with a force constant 21-98 N/m (silicon, resistivity: 0.01-0.02 Ωcm Bruker) were used for the ambient measurement.

Ellipsometry

Ellipsometry measurements were performed in the spectral range of 380 to 930 nm at the incidence of 55°, 60°, 65°, and 70°, with an ellipsometer (SENpro, SENTECH Instruments GmbH, Germany). Each data point resulted from an average of at least 5 measurements, and the obtained sensor grams were fitted with a four layer model (Si, $SiO_2$, organic layer, and air) using analysis software SpectraRay/3. The model layer of silicon VIS+NIR was used as substrate with n=3.817 and k=0.01576. The thickness of the $SiO_2$ layer was measured before coating by organic layers as a Cauchy layer and assumed to be constant (T=303.4 nm, $N_0$=1.455, and $N_1$=32.8). The organic layers were fitted by the Cauchy model.

X-Ray Photoelectron Spectroscopy (XPS)

The XPS spectra for planar surfaces were taken using a Kratos system with the following acquisition parameters: base pressure $4 \times 10^{-10}$ mbar; sample neutralization applying low energy electrons (up to 5 eV); hybrid mode (electrostatic and magnetic lenses are used), for acquiring detail spectra, and electrostatic mode for obtaining substrate signal intensities for evaluating adsorbate layer thickness; take off angle of electrons, 0°; pass energy, 20 eV in high resolution spectra and 160 eV in survey spectra; and excitation of photoelectrons by monochromatic Al $k_\alpha$ radiation (hv=1486.6 eV), which was used at 300 W (15 kV×20 mA). The analysis area was elliptically shaped with main axes of 300 µm×700 µm.

The thickness of the coatings was calculated by the attenuation of substrate (such as Ti2p, Si2p, $Au4f_{7/2}$) signals. Performing such calculation, the coatings were assumed as homogeneously packed with the same thickness in all positions. According to the take-off angle 0°, the equation of d=−ln(y)×λ can be employed, in which d is the thickness of the coatings, y is the intensity ratio obtained when comparing the peak areas of the modified and the bare substrate, and λ is the inelastic mean free path of the electrons in the polymer material of the coatings (2.8 nm for Ti2p, 3.2 nm for Si2p, and 3.3 nm for $Au4f_{7/2}$).[16]

The XPS spectra for the PG-CatPh coated TRGO nanointerface were conducted by the similar method as the planar surfaces. The TRGO and PG-CatPh-TRGO water dispersion was deposited onto the Silicon substrate with a 5 µm thickness thin film. The measurements were conducted at the take-off angle of 70°, the estimated scanning depth is about 5-7 nm. The X-ray source was run at a power of 300 W (15 kV×20 mA). Binding energies were calibrated by using the containment carbon (C1s=284.7 eV). Survey spectra were run in the binding energy range of 0-1000 eV and the high-resolution spectra of C1s, N1s, and S2s were collected.

Transmission Electron Microscopy (TEM)

Droplets (~5 µL) of sample solution were placed on carbon film coated copper grids and supernatant liquid was removed by blotting with a piece of filter paper. The grids were allowed to air-dry at least 40 min and were subsequently transferred into Philips CM12 transmission electron microscope using a standard sample holder. The investigations were performed according to the microscope low dose protocol at a calibrated primary magnification of 58,300× and an accelerating voltage of 100 kV (LaB6-illumination). All images were recorded on Kodak SO-136 electron image film with a defocus of −300 nm.

Dynamic Light Scattering (DLS) and Zeta Potential

DLS measurements were obtained using Malvern Zetasizer Nano ZS. All samples were measured at a constant scattering angle of 173° at 25° C. and freshly prepared just before measurement in PBS buffer (1 mM, pH 7.4) for the hydrodynamic size and zeta-potential measurements.

Quartz Crystal Microbalance (QCM) with Dissipation

Quartz crystal microbalance (QCM, Q-Sense E1, Sweden) with dissipation was used to test the adsorption on the surfaces. QCM allows the monitoring of changes in resonance frequency (Δf) and dissipation (ΔD) of a piezoelectric quartz crystal as a function of time. f and D were recorded at the fundamental frequency (4.95 MHz) and its third, fifth, seventh, ninth, 11th, and 13th overtones. Only the third overtone was shown in the sensor grams.

For the immobilization of catechol functionalized PGs (PG-CatPh, PG-Cat, PG-Ph, PG-A and PG-Cat(r)), the cleaned sensors were inserted into the flow chamber (QFM 401, Q-Sense, Sweden, internal volume of 40 µL) and incubated in pH 6 3-(N-morpholino) propanesulfonic acid buffer (MOPS, 0.1 M) buffer with a flow rate of 0.1 mL/min. After baseline equilibration in the buffer, a solution of PGs (1 mg/mL in MOPS buffer) was pumped into the flow chamber (0.1 mL/min). After 1 h of dynamic online adsorption, the flow chamber was alternately rinsed with MOPS buffer, aqueous solution of SDS 1% (w/w), MOPS buffer and Milli-Q water (0.1 mL/min). But for the PS sensor, the PS layer cannot keep stable in SDS solution. So, the surfactant used after MOPS buffer washing was 1% deconex (w/w, Borer Chemie AG, Switzerland) instead of 1% SDS solution. The whole measurement was performed at 25° C. The Sauerbrey equation was used to calculate the mass of the adsorbates (Δm=C×Δf, where Δm is the change in mass, C is the mass sensitivity constant of the quartz crystal (−17.7 $ng \cdot cm^{-2} \cdot Hz^{-1}$), and Δf is the overtone-normalized frequency change). It must be emphasized that alkylated and fluorinated self-assembled monolayers on Au sensors were prepared via the self-assembly of 3,3,4,4,5,5,6,6,7,7,8,8,8-tridecafluoro-1-octanethiol and 1-octanethiol on sensors, respectively.

The protein adsorption was measured similarly. The coated sensors were inserted into the flow chamber and incubated in pH 7.4 HEPES (0.1 mol/L HEPES, pH 7.4, and 150 mmol/L NaCl) buffer. After baseline equilibration, SDS (1% w/w in HEPES buffer) was pumped into the flow chamber for 10 min, followed by rinsing with HEPES buffer for 15 min. Then the protein solution (1 mg/mL, Fib, 340 kDa, pI 5.5) was pumped into the flow chamber. After 30 min, the surface was rinsed with HEPES buffer again for another 15 min. The flow rate used for all experiments was 0.1 mL/min, and the temperature was 25° C. The Voigt model for viscoelastic layers was used to calculate the mass of adsorbed proteins with the help of the software package Q-tools (version 3.0.15.553, Q-Sense, Sweden), because the D/f ratio is not small enough to consider the surfaces as rigid surfaces. The density of the adsorbed Fib layer was assumed to be 1200 kg m$^{-3}$, the fluid density to be 1000 kg m$^{-3}$, and the fluid viscosity to be 0.001 kg ms$^{-1}$.

Long-Term Stability Tests

The stability of the PG-CatPh coatings in physiological solution was monitored by Fib adsorption, thickness change, and water contact angle change. The Fib adsorption on freshly coated TiO$_2$ QCM sensors was tested by QCM, and SDS (1% w/w) was used to clean the Fib from the sensor surfaces (monitored by QCM). Then the sensors were further incubated in HEPES buffer for 1 week or 1 month (30 days) before measuring the Fib adsorption again by QCM. The coated PS QCM sensors were tested similary, but the SDS was changed to deconex (1% w/w) for cleaning.

The long-term stability of the coatings on TiO$_2$ (polar substrate) and PS (non-polar substrate) was also monitored by the water contact angle. The PG-CatPh coated TiO$_2$ and PS slides were immersed into PBS buffer (pH 7.4) or SDS solution (2%, w/w) for 1week, 1 month, and 2 month. The water contact angles were measured afterwards. Besides long-term stability, the stability of the PG-CatPh coatings on PS, PP, and SiO$_2$ wafer in sonication were also measured.

The thickness of the crosslinked and non-crosslinked coatings on SiO$_2$ wafers was measured by Ellipsometry before and after washing by surfactant.

Cell Resistance

Cell resistant experiments on PG-CatPh coated TiO$_2$ slides and tissue culture polystyrene (TCPS) wells were done with adherent NIH-3T3 murine fibroblast cells (ACC no. 59, DSMZ, Braunschweig, Germany). Cells were collected from Petri dishes by incubation in trypsin (dilution 1:250) for 5 min at 37° C. The trypsin was removed from cell suspension by centrifugation, the top layer was removed, and the remaining cells were re-suspended in a fresh medium. The TiO$_2$ slides were incubated with 40,000 cells in 3 mL of cell medium (cell number was determined via a Neubauer chamber) for 3 days at 37° C. and 5% CO$_2$. The wells of the 48-well cell culture plates were coated to test the coatings on TCPS. 1 mL cell medium with 5,000 cells was added into each coated/uncoated well. The incubated time was the same as the experiments with TiO$_2$ slides. The adhering cells were observed by microscope directly (TELAVAL 31, Zeiss, Germany), without removing the medium or rinsing the slides with PBS buffer.

Cell Adhesion

MC3T3-osteoblasts were cultured in MEM alpha media supplemented with 10% fetal bovine serum at 37° C. and 10% CO$_2$, and were harvested by the same methods as described above. Only cells at passage 7-11 were used. The bare and coated PTFE slides were incubated with 10,000 cells in 2 mL cell medium at 37° C. and 5% CO$_2$.

After 24 hours, the cells were rinsed with PBS buffer and fixed with 4% paraformaldehyde for 15 min and were treated with 0.25% (v/v) Triton X-100 for 10 min for permeabilization. After passivated the samples with 1% (w/v) bovine serum albumin (BSA) for 45 min, the samples were incubated with the primary antibody, mouse anti-paxillin (clone 349, 1:300 dilution, 610051, BD Biosciences, USA) for 60 min and followed by the incubation with anti-mouse secondary antibody tagged with the fluorescent dye Alexa Fluor 488 (1:300 dilution, Abcam, Germany) for the other 60 min. The filamentous actin and nucleus were labeled with Alexa Fluor 568 conjugated phalloidin and 4',6-diamidino-2-phenylindole (DAPI) respectively, for 30 min.

Summarizing, a universal monolayer coating is provided that is independent on the composition, size, shape, and structure of the substrates. It has been demonstrated that the PG-CatPh polymers are uniformly and robustly coated on both macro-scale planar surfaces and nanosystems. The exposed hydrophilic moieties of the coatings hinder the formation of uncontrollable multilayers or agglomerates. Therefore, the universal coating ability of the polymers is suitable for macro/nano-interfaces. In addition, the antifouling performance of the coatings was proven on TiO$_2$ and PS to prevent unspecific protein adhesion, while specific interactions were shown by cellular adhesion and spreading on PTFE surface. Therefore, this universal monolayer coating provides a new platform for material surface modification and can be used in a wide range of biointerface applications.

Exemplary Embodiment: Amphiphilic Block Copolymer with Polyglycerol as Hydrophilic Block and Benzophenone as Reactive Group of the Crosslinking Domain (PG-BPh)

Figure 17:
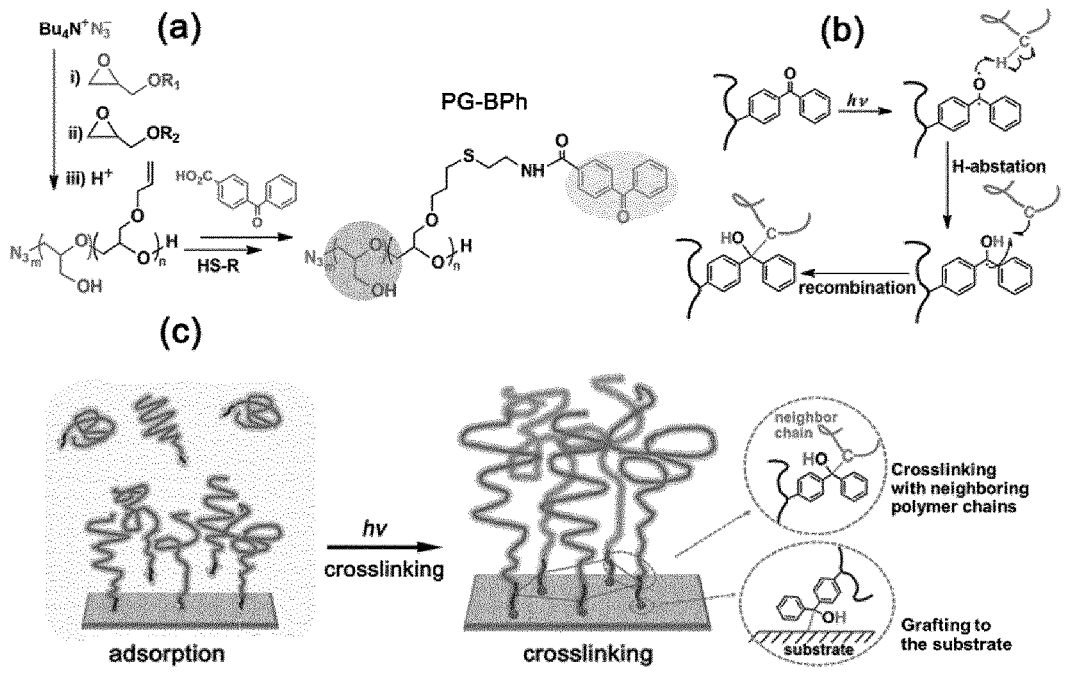
FIG. 17a is a schematic depiction of a manufacturing process of PG-BPh as an embodiment of the coating compound as well as of an exemplary application of PG-BPh.
FIG. 17b shows the chain insertion crosslinking mechanism of benzophenone group under UV irradiation.
FIG. 17c shows PG-BPh brush coatings fabricated from PG-Ph.

This exemplary embodiment relates to at a new polyglycerol (PG)-based bifunctional amphiphilic block copolymer with reactive anchors/crosslinkers that rapidly generate a stable polymer coating on various nonpolar surfaces in a non-invasive manner. Benzophenone (BPh), a traditional photo initiator and crosslinker, was incorporated into the block copolymer as an excellent crosslinkable anchor due to its affinity to hydrophobic substrates/see FIGS. 17a and 17b). The well-defined BPh functionalized, PG-based block copolymers with multiple BPh in the anchoring units block were first adsorbed on substrates with high density. In the second step, the BPh groups were covalently linked with substrates and/or neighboring polymer chains via photo-induced grafting and crosslinking (FIG. 17c). Thus, PG-BPh brush coatings were fabricated via an "adsorption-crosslinking" approach based on a sequence of versatile photo-initiated C—H insertion crosslinking steps. BPh groups serve as hydrophobic domains in the first "Adsorption" step and further contribute to surface anchoring and/or intralayer crosslinking during UV irradiation in the second "Crosslinking" step. The ω-N$_3$ terminal groups in the bifunctional amphiphilic block copolymer serve as in situ modification sites.

The intralayer crosslinking combined with the weak hydrophobic interaction at the interface facilitated to obtain a polyvalent anchoring on the substrates that lack aliphatic C—H groups (i.e., PTFE). The resulting PG-BPh coatings showed excellent protein and cell resistance, which required and reversely indicated the high density of the polymer brushes as described above. The antifouling performance was maintained for at least one year in the physiological buffer, which benefited from the stably anchoring and high thermal and oxidative stability of the polymer backbone. Although a set of mussel-inspired universal coatings was designed in previous studies,[9, 24] the protein resistance on coated hydrophobic nonpolar substrate (e.g., PS) surface never reached the same low level as on TiO$_2$ surface. The ongoing challenge of achieving such low fouling on nonpolar surfaces was only mastered by the newly developed PG-BPh, which allows an application as antifouling coatings. Moreover, the PG-BPh coating is "ready-to-use" for post modification profiting from the defined w-terminal groups. Purposely-designed $N_3$ terminals were in situ functionalized with glyco-ligands, e.g., mannoses that, on the one hand, specifically adsorb lectins by multivalent protein carbohydrate interactions and, on the other hand, still prevent the nonspecific adsorption of other proteins.

Synthesis of Amphiphilic Block Copolymer

The PG-BPh bifunctional amphiphilic block copolymer was synthesized via the ring-opening anionic polymerization of ethoxyethyl glycidyl ether (EEGE) and allyl glycidyl ether (AGE), followed by acetal deprotection, thio-ene amination with cysteamine and BPh linking by amide formation. The amount of the grafted BPhs was verified to guarantee an optimal coating density and brush conformation of the adsorbed polymers from aqueous solution (1 mg/mL). With the increase of BPh content in the polymer chain, the thickness of the resulting coatings on PS surface gradually increased and reached a plateau value at approx. 3.2% (in mole ratio) BPh content, corresponding to ~4 BPh units per polymer chain. At this BPh content, the water contact angle (WCA) plot exhibited an inflection point. The surface hydrophobicity decreased before reaching this point and increased hereafter. This indicates that a change of the internal layer structure occurs at this point (WCA of 63°±1°) and suggests that the layer termination is dominated by PG based chains. Apparently, a certain amount of BPh was required to generate enough hydrophobicity at the interface, but too many BPh units would increase the steric effect and result in a less dense coating. Therefore, in the following the block copolymer with 4 BPh units was utilized unless otherwise specified.

Figure 18:
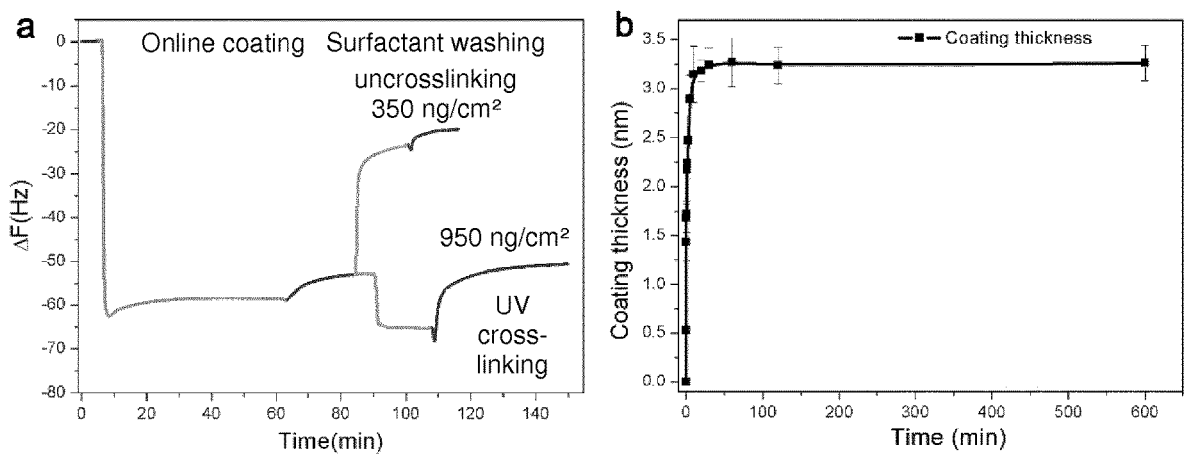
FIG. 18a shows the QCM frequency shift as a function of time during the adsorption of PG-BPh on a PS sensor surface.
FIG. 18b shows the ellipsometric thickness of PG-BPh polymers on PS substrates with the evolution of the coating time.

In a block-selective solvent ($H_2O$), which is good for the PG block but poor for the BPh block, pristine substrate surfaces were exposed, and an adsorbate layer was formed. Quartz crystal microbalance (QCM) with dissipation was employed to analyze the adsorption of the polymers on PS sensors. The results show that the hydrated mass of the adsorbed PG-BPh on the sensor surfaces was about 950 ng/cm$^2$ (FIG. 18a). Thereby, FIG. 18a shows the QCM frequency (f) shift as a function of time during the adsorption of PG-BPh on a PS sensor surface. The curve between ca. 65 and 85 minutes as well as the upper curve after ca. 100 minutes and the lower curve after ca. 110 minutes show buffer rinsing. The curve from ca. 0 to 65 minutes indicates physisorption of amphiphilic block copolymer and the curves between ca. 85 minutes and ca. 100 minutes (upper curve) or ca. 110 minutes (lower cureve), respectively, demonstrate the surfactant washing.

However, the polymers only weakly adsorbed onto the PS substrate and were easily rinsed away by surfactant solutions. Nearly 65% of the adsorbed polymers detached after rinsing with 1% w/w deconex aqueous solution (FIG. 18a, upper curve). This result was expected and agreed with the properties of adsorbates formed by traditional amphiphilic polymers. However, when the freshly deposited coatings were exposed to UV-irradiation (365 nm, 42 mW/cm$^2$), the obtained coatings maintained stable upon rinsing with surfactant solutions (FIG. 18a, upper curve, and FIG. 18b). Thereby, FIG. 18b shows the ellipsometric thickness of PG-BPh polymers on PS substrates with the evolution of the coating time.

Under UV irradiation, the BPh groups underwent a n–π* transition into a triplet state and abstracted a hydrogen atom from neighboring aliphatic C—H groups, i.e., from either the substrate or the neighboring polymer chain,[25, 26] which resulted in a covalent C—C bonding with the substrate or the neighboring polymer chain (cf. FIG. 17c). The optimized UV-irradiation time was identified by a decrease in WCA and increase in coating stability under subsequent rinsing with deconex. Only 30 seconds of irradiation was sufficient to covalently immobilize the polymers onto PS substrate and/or completely crosslink the polymer chains. The first step of polymer diffusion onto the solid substrates allowed a very fast layer preparation/formation. As indicated by ellipsometry (FIG. 18b), the dry thickness reached a plateau value with approx. 3.5 nm in 3 min. As this value did not increase even after immersion times up to 10 hours, it is concluded that the respective surface coverage corresponds to the equilibrium surface grafting density. The grafting density of polymer chains was calculated according to the following equation: [27]

$$\sigma = (h\rho N_a)/M_n$$

where h is dry the thickness of the coating, $\rho$ is the bulk density of the coating polymer (assumed to be 1.1 g/cm$^3$ for PG-BPh), Na is Avogadro number and Mn is the number average molecular weight of the polymer. The resulting equilibrium coating density was about 0.2 chains/nm$^2$, which was in the scale of a dense monolayer brush coating and significantly higher than previously reported "grafting to" brush coatings.[28, 29, 30]

As mentioned above, the generated radicals from BPhs can randomly insert any neighboring aliphatic C—H group and form covalent C—C bonds, regardless of the coating polymer and the substrate. Therefore, the PG-BPh coatings displayed substrate independent properties. The static water contact angles of all the tested surfaces, significantly decreased after the coating as expected. Following the UV-treatment, the PG-BPh polymers were even effectively tethered onto chemical inert PDMS and PTFE, which are otherwise hard to coat. The stability of the PG-BPh coatings was investigated on selected substrates, namely PS, PP and PTFE. The contact angles of the PG-BPh coated surfaces did not obviously increase after incubation in a SDS solution (2%, w/w) for 30 min under sonication.

Figure 19:
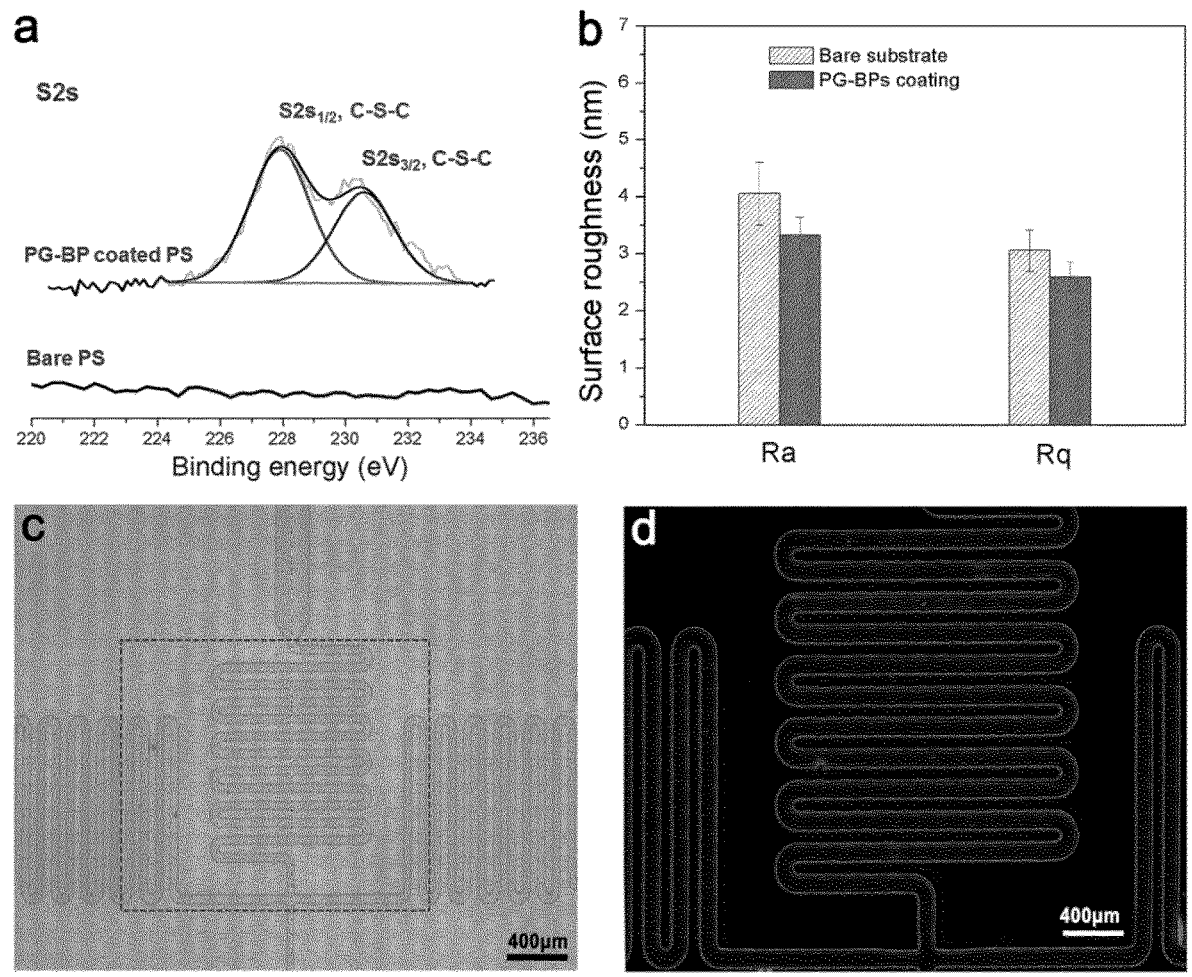
FIG. 19a shows deconvoluted XPS S2s signal curves of PG-BPh coatings on PS substrate and the corresponding curves of pristine PS substrate.
FIG. 19b shows average surface roughness for bare and coated PS surfaces.
FIG. 19c shows an image of a microfluidic chip made of PDMS.
FIG. 19d shows a fluorescence image of the microfluidic chip of FIG. 19c after PG-BPh coating.

The chemical composition of PG-BPh coatings on PS substrates was confirmed by X-ray photoelectron spectroscopy (XPS) analysis. The deconvoluted S2s spectra for PG-BPh coating and the corresponding pristine PS substrate is shown in FIG. 19a. The significant S2s peaks, ascribed to the sulfur of sulfide bond (cf. FIG. 17a), were only detected in case of substrates covered with PG-BPh polymer coatings but not in case of pristine substrates. This finding confirms the successful polymer coating.

The surface morphology of the coatings and the respective bare substrates was investigated by atomic force microscopy (AFM). On the coated substrates, island-like structures could be clearly observed, and this morphology was construed typical of monolayer polymer brush coating.[10] The monolayer coatings were ultra-smooth and ultra-thin. Both the average roughness ($R_a$) and root-mean-square roughness ($R_q$) of the coatings were slightly smaller than those of the bare PS substrate (FIG. 19b). The roughness was calculated from 5 AFM images (2×2 μm$^2$). It is assumed that the coating levels the grooves of the substrates. The coating thickness under ambient condition was 3.6±1.0 nm as measured by AFM and correlated well with the ellipsometry research (FIG. 18b).

Besides the coating on 2D planar surfaces, the polymers can also be efficiently used for the complex 3D systems including PDMS microfluidic chips (FIGS. 19c and 19d), polyethylene microtubes, as well as PVC blood platelet storage bag by simple dip-coating. Thereby, FIG. 19c shows an image of a microfluidic chip of PDMS. FIG. 19d shows the corresponding fluorescence image after PG-BPh coating. The PG-BPh polymer used here was covalently modified with 2% (to OH groups in backbone) fluorescein isothiocyanate (FITC) prior to coating, leading to fluorescing PG-BPh. The light grey lines on the surface of the channel extending through the microfluidic chip originate from the fluorescing PG-BPh.

It is noteworthy that the PG-BPh coatings were also successful on polar inorganic surfaces (including gold, titania, and silica) because of the crosslinkable BPh anchors.

Figure 20:
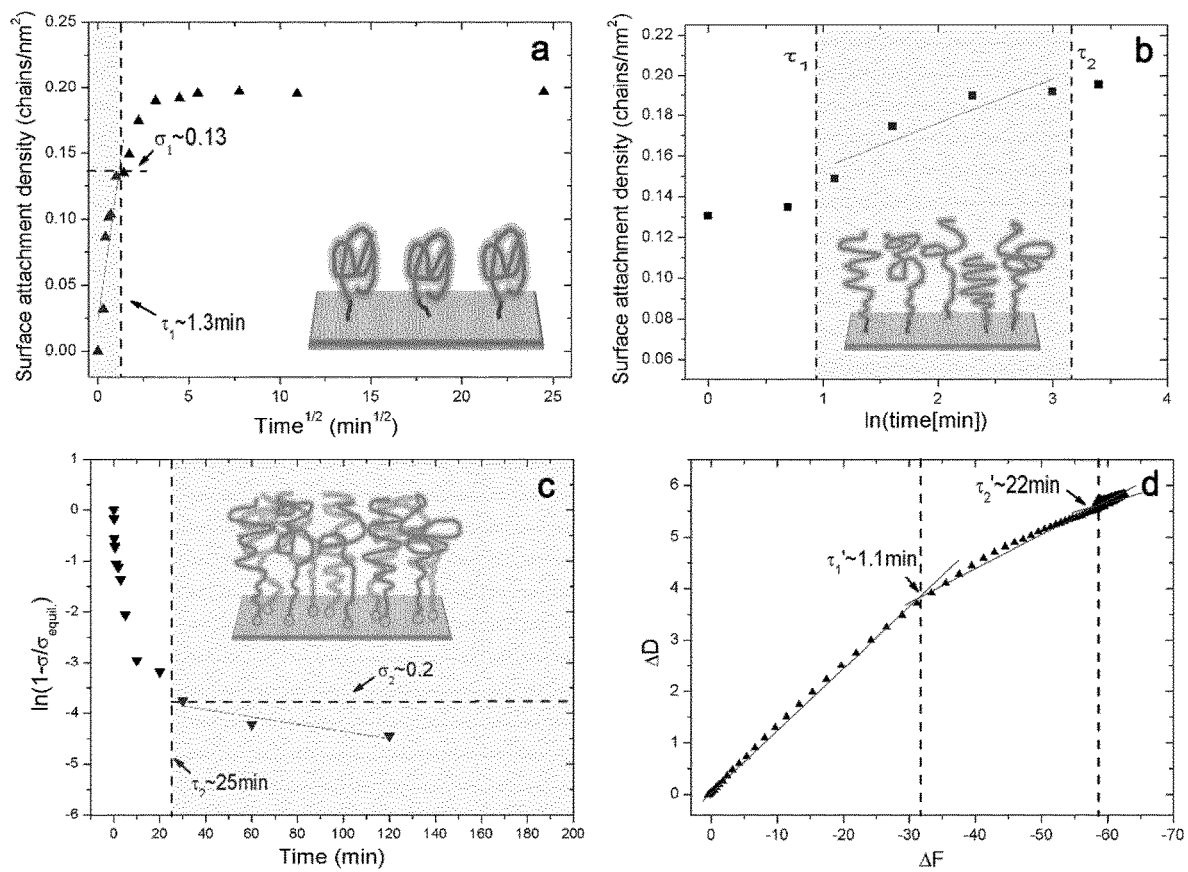
FIG. 20a shows the grafting density of PG-BPh polymers as a function of $t^{0.5}$ in the diffusion-controlled region.
FIG. 20b shows the dependence of the grafting density of PG-BPh in the crossover regime.
FIG. 20c shows the grafting density of PG-BPh as a function of time in the terminal regime.
FIG. 20d shows $\Delta D$-$\Delta f$ plots of the adsorption of PG-BPh on PS sensor surfaces.

Kinetics of Brush Formation. The adsorption of polymer chains from dilute solution to the impenetrable solid surface to form a monolayer of polymer brushes has been extensively studied.[31-34] According to the hypothesis of Ligoure and Leibler,[35] the initial tethering regime (diffusion regime) for an end-functionalized polymer attached to a substrate surface should be diffusion controlled and exhibit a $t^{0.5}$ dependence on the tethering time. The diffusion of polymer chains from solution to the substrate surface is comparably fast. The tethering rate of PG-BPh onto a PS substrate surface in the diffusion regime corresponded well to the prediction as shown in FIG. 20a. During the first 1.3 min, the surface grafting density (a) exhibited a linear relationship with $t^{0.5}$. The characteristic time $\tau_1$ is obtained from the inflection point of the fitting curve and indicates the end of the first kinetic regime. The corresponding areal density of polymer chains on the substrate surface is $\tau_1$. The average distance between tethering sides on the substrate was defined as d, which can be calculated from the experimental values of σ following the equation: $d=(\sigma\pi/4)^{-1/2}$.[31] The value of d at the end of the diffusion regime was 7.7 nm, which is far larger than the gyration radius ($R_g$) of PG-BPh polymers (that is 1.7~1.8 nm for polyglycerol with molecular weight 10 kDa [36]). According to the commonly used criterion [31] it may be expected that for $d>2R_g$ the tethered polymer chains have sufficient lateral space on the substrate surface and should be in an expanded coil or mushroom conformation. Therefore, a layer of non-overlapping and relaxed polymer chains covered the substrate in the first coating regime.

When the grafting density further increased, the tethering rate progressively slowed down and was proportional to ln(t) due to the increased energy barrier (FIG. 20b). This coating regime was controlled by the diffusion of free polymers through the already tethered chains to reach the substrate surface. This slow tethering was expected to continue until saturation. At this point, the energy/enthalpy benefits of adsorbing polymer chains to the surface would be offset by the entropic cost of chain stretching. [32, 35] In this period, the d gradually decreased and finally was lower than $2R_g$. The gradually increased areal density of chains on the substrate surface would result in lateral compression of the adsorbed polymer chains and stretching them away from the surface to avoid an overlap.[35] Therefore, there was an obvious conformation transition of the tethered polymer chains from mushroom to brush. At the end of regime two ($\sigma_2$=0.2, d=2.24 nm <$2R_g$=3.5 nm), most of the tethered polymer chains were in a moderately-dense and extended conformation (FIG. 20c).

Following the conformation transition, there was a terminal kinetic regime, where only a small amount of polymers could be tethered onto the surface due to the penetration barrier. The polymers tethering kinetics exhibited a penetration-limited behavior. As shown in FIG. 20c, the natural logarithm of the normalized tethering rate, $\ln[1-\sigma(t)/\sigma_{equil}]$, displayed an almost linearly progressive declination with time as predicted for a penetration barrier.[35] The declining rate was associated with a progressive increase in the penetration barrier during the tethering procedure and a dense polymer brush layer built up. Thus, the pre-attached polymer chains were further stretched up because of an increased chain density. Finally, a highly dense monolayer brush coating was generated. In summary, the adsorption kinetics of the PG-BPh block copolymers to the PS substrate exhibited three regimes: (i) the diffusion-controlled regime where σ(t) was dependent on $t^{0.5}$; (ii) regime where σ(t) slowly increased with ln(t) and was accompanied with a conformation transition of the adsorbed polymers from mushroom to brush, and finally (iii) penetration-limited regime where the areal density of polymers displayed a linearly progressively increase with time to obtain the final highly dense brush coatings.

The adsorption model of PG-BPh polymers onto PS substrate was also investigated by evaluating the ΔD versus Δf graphs during the adsorption processes via QCM online coating data (60 minutes online coating). The starting point of the dynamic coating process was defined as ΔD=Δf=t=0. The ΔD versus Δf plot of the polymer adsorption displayed three phases with significantly different slopes (FIG. 20d). The slope of the first phase (|∂D/∂f$_1$|=0.12) was significantly greater than the second phase (|∂D/∂f$_2$|=0.06). This indicated that loosely bound coatings that were formed in the first phase with flexible polymer chains were accompanied by a large amount of hydrodynamically coupled water.[7] The inflection point between these two phases was about −31.6 Hz, which corresponded to t=1.3 min ($\tau'_1$) and exactly matched the end time for the diffusion-controlling regime. Following the second phase, a third phase with a smaller slope (|∂D/∂f$_3$=0.02) appeared where ΔD only slightly increased with an increase of |Δf|. The adsorbed polymers in this phase were likely to compact the coating in such a way that the trapped water was replaced by additional polymer chains,[8] which resulted in highly dense coatings. The break point ($\tau'_2$) between these two phases was at 22 min, which coincided with the onset time of the penetration-limited regime as well.

Figure 21:
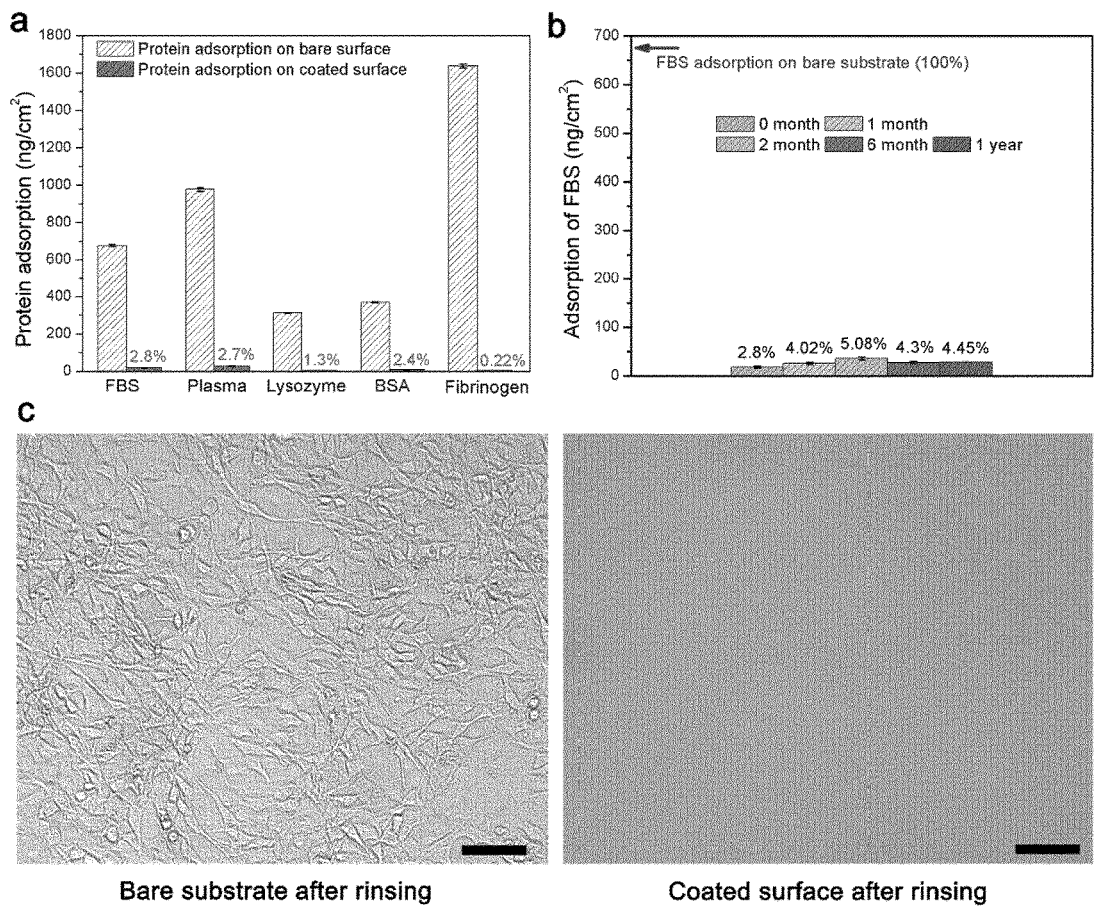
FIG. 21a shows protein adsorption on PG-BPh coated PS surfaces.
FIG. 21b shows protein adsorption from FBS to the coated PS surfaces before and after incubation in PBS buffer for 1 month, 2 months, 6 months and 1 year.
FIG. 21c shows NIH3T3 cell adhesion on the PG-BPh coated PS and the pristine surface after 3 days of cell culture.

Antifouling Performance. After successful monolayer characterization, the protein resistance of the PG-BPh coating was evaluated by single proteins including fibrinogen (Fib), bovine serum albumin (BSA), and lysozyme (Lys), as well as by the complex protein environment of undiluted fetal bovine serum (FBS) and human blood plasma. As indicated by QCM studies, the coatings exhibited an extremely high protein resistance (FIG. 21a). The coated PS surface successfully repelled >97% of the adsorbed single proteins relative to the bare PS surfaces. More notably, Fib, a large protein presents in relatively large quantities in the blood and strongly adsorbs to hydrophobic surfaces, was repelled till <0.2%. Only <4 ng/cm$^2$ Fib (including the mass of the associated water) was adsorbed onto the coated surfaces, which is comparable with the benchmark protein-resistant system that was generated by surface polymerization on gold surfaces and evaluated by surface plasmon resonance (SPR, the mass of the associated water was excluded).[37] Most impressively, the proteins in FBS and blood plasma were effectively repelled as well. Only 2.8% adsorbed on the PG-BPh coated PS, whereas more than 10% adsorbed on an universal monolayer [24] and even more than 20% adsorbed on multilayer coated PS [9] in previous studies of the inventors. This excellent protein resistance can be explained by the highly hydrated and densely packed PG brushes, which exhibited highly flexible aliphatic polyether backbone with multiple hydrophilic functional groups as well as high thermal and oxidative stability, has been proven to have high affinity with water molecules to generate a hydration layer.[9, 24] The hydration layer serves as an efficient barrier to non-specific protein adsorption.[18, 19, 38] Moreover, the coatings were very stable over time and they still resisted >95% of the proteins from FBS even after incubation in physiological buffer for 1 year (FIG. 21b), which benefited from the stably anchoring and high thermal and oxidative stability of the polymer backbone. Specifically, FIG. 21b shows protein adsorption from FBS to the coated PS surfaces before and after incubation in PBS buffer for 0 months, 1 month, 2 months, 6 months and 1 year (bars from left to right).

Mammalian cell adhesion on surface is known to be mediated by the adsorption of extracellular matrix (ECM) proteins.[39] Therefore, the protein-resistant surfaces are likely to be cell-resistant as well. Cellular resistance of the PG-BPh coated surfaces was evaluated by NIH3T3 mouse fibroblasts, which are involved in the tissue responses upon implantation into living tissue.[40] NIH3T3 cells were cultured for three days on the coated PS (FIG. 21c), PP, and PVC slides as well as the related bare references (the scale bars corresponds to 50 μm). Cells grew to confluence on the bare surfaces (PS, PP, and PVC) after only three days, whereas only a few and evidently unspread cells sedimented to the coated surfaces before rinsing, and almost no cells (<1) attached after gentle rinsing with PBS.

Figure 22:
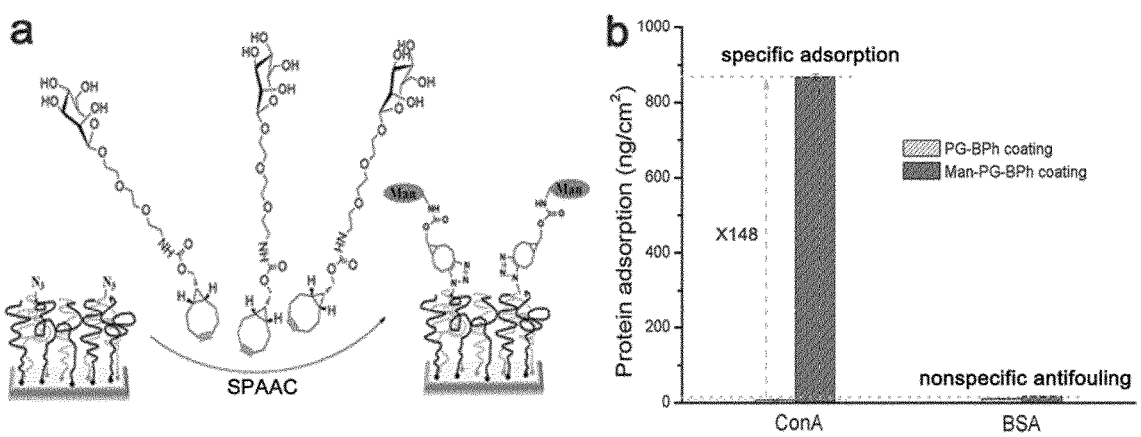
FIG. 22a shows a scheme of grafting Man onto PG-BPh coatings via SPAAC.
FIG. 22b shows specific adsorption of ConA and unspecific resistance of BSA on Man-modified PG-BPh coatings investigated by QCM.

Biospecific protein adsorption and bacteria capture. The presented nonspecific antifouling surfaces provided an excellent bioinert background for the biospecific adsorption of desired proteins. α-D-mannose (Man), which is a key component of the glycochain on the cellular surface,[41] was grafted onto PG-BPh coatings via in situ strain-promoted azide-alkyne cycloaddition (SPAAC) [12] between the azide terminal groups on the brush chain and a cycloalkyne functionalized mannose. The yield of the in situ SPAAC on the coated surface was very high, whereby at least 95% of the azide terminal groups of PG-BPh brushes were reacted with Man-BCN. After immobilization, about 890 ng/cm$^2$ concanavalin A (ConA), which contains a Man bining site,[42] was conjugated onto the coatings and measured by QCM (FIGS. 22a and 22b). By comparison, only about 6 ng/cm$^2$ (148 folds lower) adsorbed on the coatings without Man (FIG. 22b). Additionally, the immobilized Man did not obviously increase the adsorption of BSA.

Figure 23:
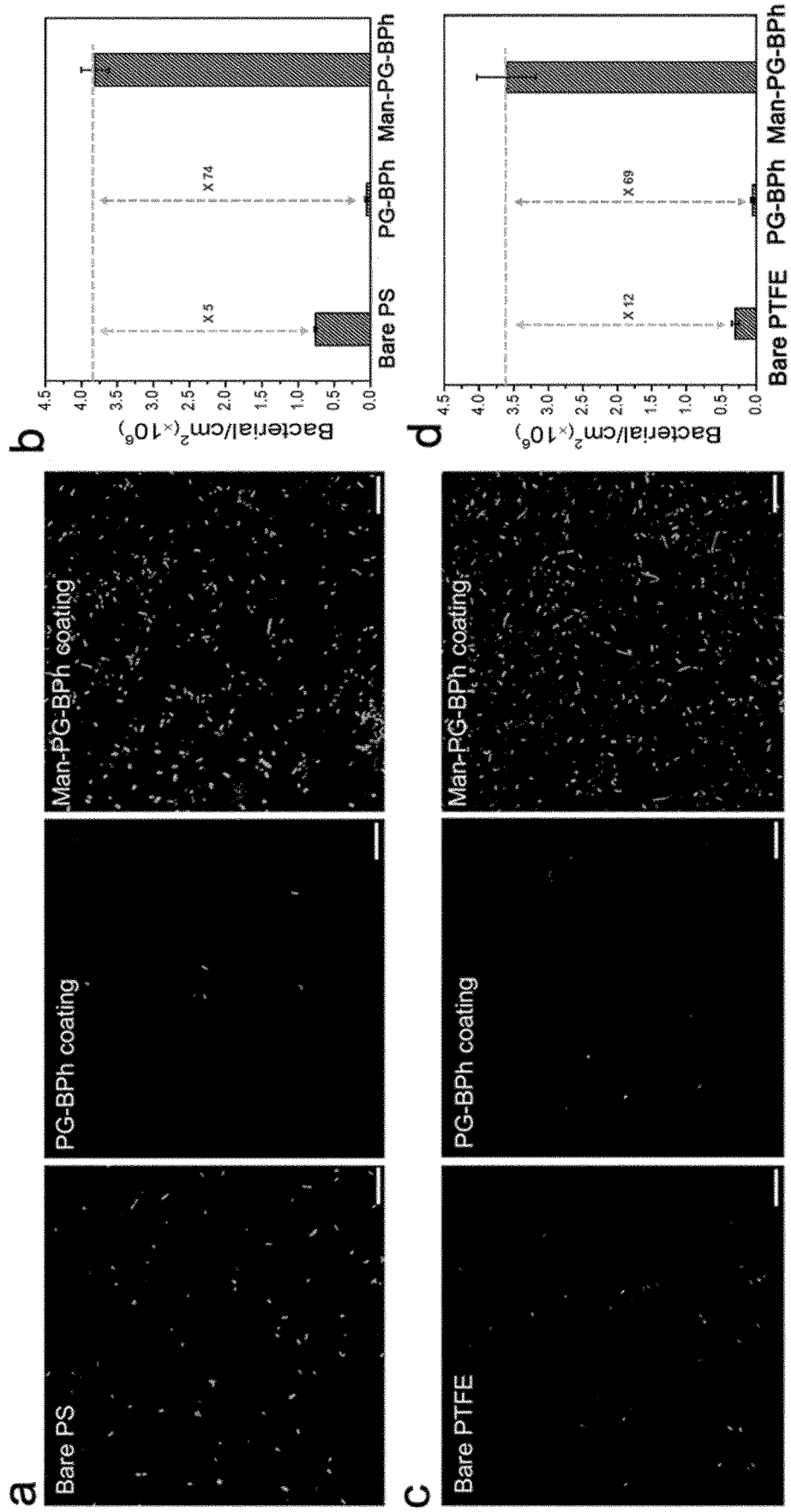
FIG. 23a shows biospecific capture of E. coli on bare, PG-BPh coated and Man-PG-BPh coated PS surface.
FIG. 23b shows the number of E. coli that adhere on bare, PG-BPh coated, and Man-PG-BPh coated PS.
FIG. 23c shows biospecific capture of E. coli on bare, PG-BPh coated and Man-PG-BPh coated PTFE surface.
FIG. 23d shows the number of E. coli that adhere on bare, PG-BPh coated, and Man-PG-BPh coated PTFE surfaces.

An *E. coli* biofilm development is a complex process that is important for disease and for engineering applications. [43] The conjugated Man ligand can mediate and promote the specific adhesion of mannose-specific (MS) bacteria such as *E. coli*, *Klebsiella pneumoniae*, and *Salmonella* spp.[44] This attachment is mediated by bacterial surface lectins in the form of type 1 fimbriae, which are terminated by an α-D-mannose specific lectin named FimH.[45] These type 1 fimbriae are expressed in several hundred copies on the bacterial cell surface to achieve tight adhesion through multivalent protein carbohydrate interactions. After incubating with *E. coli* suspension for 10 h, a large number of bacteria attached and formed a monolayer biofilm onto the Man-PG-BPh modified PS (FIGS. 23a and 23b) and PTFE (FIGS. 23c and 23d) surfaces, while only a few cells could be observed on the bare and PG-BPh coated surfaces. Therefore, this *E. coli* specific capture coating could be utilized in many biotechnological fields, including applications in the filtration of drinking water, the degradation of wastewater and solid waste, and biocatalysis in biotechnological processes, such as the production of bulk and fine chemicals, as well as biofuels microbial fuel cells.[46, 47]

Experimental Section: Coating. Polystyrene (PS), Polytetrafluoroethylene (PTFE), Polypropylene (PP), Polyvinyl chloride (PVC), Polyethylene terephthalate (PET), Polyurethane (PU), and Polydimethylsiloxane (PDMS) slides (1×1 cm$^2$) were cleaned ultrasonically in isopropanol and water. The TiO$_2$ slide was cleaned ultrasonically in water and methanol firstly, and then treated with UV-ozone (UV/ozone ProCleaner, Bioforce Nanosciences) for 20 min before using. The SiO$_2$ was cleaned by freshly prepared piranha solution (H$_2$SO$_4$/H$_2$O$_2$=3:1) for 30 min, followed by successive rinsing with Milli-Q water and methanol. Gold slides were also cleaned by piranha solution but for 30 s. All the QCM chips were cleaned according to the standard cleaning protocol from LOT (LOT-Quantum Design GmbH, Darmstadt, Germany).

To prepare PG brush coatings, the cleaned slides were immersed into a solution of 1 mg/mL PG-BPh in Milli-Q water at room temperature for 2 h. After that, the slides were thoroughly rinsed with Milli-Q water and then dried by N$_2$ stream. The coated slides were put under a LED UV lamp (365 nm, 30 mW/cm$^2$) and irradiated for 30 s. For the surface's post-modification, crosslinked coating slides were dipped into a 10 mM Man-BCN methanol solution and shaken for 3 h at room temperature. The slides were thoroughly rinsed with methanol and Milli-Q water and then dried by N$_2$ stream. The concentration of the polymer solutions for coating was always 1.0 mg/mL, which was far smaller than the critical micelle concentrations (CMC) of PG-BPh polymer (>100 mg/mL). It has been shown that if the concentration of amphiphilic block copolymer was higher than the CMC, the block copolymer would form micelles in the selective solvent and the adsorbed surface layer itself may have a micellar structure instead of a smooth monolayer brush coating.[48]

The coating on 3D architectural surface was conducted in a similar operation as the coating on planar surface. The FITC-modified PG-BPh aqueous solution (5 mg/mL) was filled into a PE tube and a microfluidics chip and kept them in the dark at room temperature for 2 h. The coating on platelet storage bags was performed by immersing a piece of a platelet storage bag inside of FITC modified PG-BPh solution and stored in dark at room temperature for 2 h. After that, it was thoroughly washed with methanol and Milli-Q water and then dried by N$_2$ stream. A LED UV lamp (365 nm; 42 mW/cm$^2$) was used to initiate the crosslinking of benzophenone and the further immobilized the coating onto 3D architecture surface.

In summary, a highly dense bifunctional and long-term stable monolayer brush coating forms on various nonpolar surfaces, including the highly inert materials, PDMS and PTFE by a simple "adsorption-crosslinking" technology based on an amphiphilic block copolymer with benzophenone (BPh) as the reactive anchor. The adsorbed BPhs initiated the unselective chain insertion crosslinking reaction under short UV irradiation to immobilize the polymer chains either on the substrates presented aliphatic C—H groups via covalent bonding or on the other substrates by multivalent adsorption and covalent crosslinking. This process resulted in an ultrathin, smooth, and highly stable monolayer brush coating. Besides the coatings on 2D planar surfaces, the PG-BPh polymers can also be used to coat complex 3D systems, e.g., microfluidics channels, which extended its potential application to a lab on chip. The modified nonpolar surfaces exhibited outstanding antifouling properties, which were comparable with the benchmark antifouling coatings on polar model surfaces. After post-modification with biospecific ligands, e.g., mannose, these nonspecific antifouling surfaces were converted to highly biospecific protein adsorption and bacteria capture coatings via multivalent protein carbohydrate interactions. Therefore, this highly stable monolayer coating provides a new platform for universal material surface modification and can be used in a wide range of biointerface applications. The present proposed solution thus opens up new avenues for the modification of nonpolar material surfaces and in situ immobilization of a wide variety of selective biomolecules.

LIST OF REFERENCES CITED IN THE PRECEDING SECTIONS

[1] S. R. Meyers, M. W. Grinstaff, *Chem. Rev.* 2011, 112, 1615-1632.
[2] Q. Wei, R. Haag, *Mater. Horiz.* 2015, 2, 567-577.
[3] a] D. Y. Ryu, K. Shin, E. Drockenmuller, C. J. Hawker, T. P. Russell, *Science* 2005, 308, 236-239; b] J. Lahann, D. Klee, H. Wicker, *Macromol. Rapid Commun.* 1998, 19, 441-444; c] H. Lee, S. M. Dellatore, W. M. Miller, P. B. Messersmith, *Science* 2007, 318, 426-430; d] H. Ejima, J. J. Richardson, K. Liang, J. P. Best, M. P. van Koeverden, G. K. Such, J. Cui, F. Caruso, *Science* 2013, 341, 154-157.
[4] T. H. Anderson, J. Yu, A. Estrada, M. U. Hammer, J. H. Waite, J. N. Israelachvili, *Adv. Func. Mater.* 2010, 20, 4196-4205.
[5] Q. Wei, F. Zhang, J. Li, B. Li, C. Zhao, *Poly. Chem.* 2010, 1, 1430-1433.
[6] J. L. Dalsin, P. B. Messersmith, *Mater. Today* 2005, 8, 38-46.
[7] F. Hook, M. Rodahl, B. Kasemo, P. Brzezinski, *Proc. Natl. Acad. Sci.* 1998, 95, 12271-12276.
[8] S. Belegrinou, I. Mannelli, P. Lisboa, F. Bretagnol, A. Valsesia, G. Ceccone, P. Colpo, H. Rauscher, F. Rossi, *Langmuir* 2008, 24, 7251-7261.
[9] Q. Wei, T. Becherer, P. L. M. Noeske, I. Grunwald, R. Haag, *Adv. Mater.* 2014, 26, 2688-2693.
[10] N. Ishida, S. Biggs, *Macromolecules* 2010, 43, 7269-7276.
[11] U. Hersel, C. Dahmen, H. Kessler, *Biomaterials* 2003, 24, 4385-4415.
[12] J. Dommerholt, S. Schmidt, R. Temming, L. J. Hendriks, F. P. Rutjes, J. van Hest, D. J. Lefeber, P. Friedl, F. L. van Delft, *Angew. Chem. Int. Ed.* 2010, 49, 9422-9425.
[13] A. O. Fitton, J. Hill, D. E. Jane, R. Millar, *Synthesis* 1987, 1140-1142.
[14] Z. Qi, P. Bharate, C.-H. Lai, B. Ziem, C. Böttcher, A. Schulz, F. Beckert, B. Hating, R. Mülhaupt, P. H. Seeberger, *Nano Lett.* 2015, 15, 6051-6057.
[15] J. Ge, Y. Hu, M. Biasini, W. P. Beyermann, Y. Yin, *Angew. Chem. Int. Ed.* 2007, 46, 4342-4345.
[16] a] M. Esplandiu, P.-L. Noeske, *Appl. Surf Sci.* 2002, 199, 166-182; b] W. L. Cavalcanti, A. Brinkmann, M. Noeske, S. Buchbach, F. Straetmans, M. Soltau, *Eur. Coat. 1* 2012, 10, 1-4.
[17] T. Gillich, E. M. Benetti, E. Rakhmatullina, R. Konradi, W. Li, A. Zhang, A. D. Schlüter, M. Textor, *J. Am. Chem. Soc.* 2011, 133, 10940-10950.
[18] C. Siegers, M. Biesalski, R. Haag, *Chem.-Eur. 1* 2004, 10, 2831-2838.
[19] Q. Wei, T. Becherer, S. Angioletti-Uberti, J. Dzubiella, C. Wischke, A. T. Neffe, A. Lendlein, M. Ballauff, R. Haag, *Angew. Chem. Int. Ed.* 2014, 53, 8004-8031.
[20] M. Arnold, E. A. Cavalcanti-Adam, R. Glass, J. Blümmel, W. Eck, M. Kantlehner, H. Kessler, J. P. Spatz, *ChemPhysChem* 2004, 5, 383-388.
[21] S. Sakai, Y. Yamada, T. Zenke, K. Kawakami, *J. Mater. Chem.* 2009, 19, 230-235.
[22] M. Gervais, A. Labbé, S. Carlotti, A. Deffieux, *Macromolecules* 2009, 42, 2395-2400.
[23] J. r. Meyer, H. Keul, M. Möller, *Macromolecules* 2011, 44, 4082-4091.
[24] Yu, L.; Cheng, C.; Ran, Q.; Schlaich, C.; Noeske, P.-L. M.; Li, W.; Wei, Q.; Haag, R. *ACS Appl. Mater. Interfaces* 2017, 9, 6624.
[25] Toomey, R.; Freidank, D.; Rae, J. *Macromolecules* 2004, 37, 882.
[26] Christensen, S. K.; Chiappelli, M. C.; Hayward, R. C. *Macromolecules* 2012, 45, 5237.
[27] Iyer, K. S.; Luzinov, I. *Macromolecules* 2004, 37, 9538.
[28] Sofia, S. J.; Premnath, V.; Merrill, E. W. *Macromolecules* 1998, 31, 5059.
[29] Huang, H.; Rankin, S. E.; Penn, L. S.; Quirk, R. P.; Cheong, T. H. *Langmuir* 2004, 20, 5770.
[30] Huang, H.; Penn, L. S. *Macromolecules* 2005, 38, 4837.
[31] Huang, H.; Penn, L.; Quirk, R.; Cheong, T. *Macromolecules* 2004, 37, 516.
[32] Hasegawa, R.; Doi, M. *Macromolecules* 1997, 30, 5490.
[33] Zhang, S.; Vi, T.; Luo, K.; Koberstein, J. T. *Macromolecules* 2016, 49, 5461.
[34] Smith, G. D.; Zhang, Y; Yin, F.; Bedrov, D.; Dadmun, M.; Huang, Z. *Langmuir* 2006, 22, 664.
[35] Ligoure, C.; Leibler, L. *J. Phy. France* 1990, 51, 1313.
[36] Wen, J.; Weinhart, M.; Lai, B.; Kizhakkedathu, J.; Brooks, D. E. *Biomaterials* 2016, 86, 42.
[37] Jiang, S.; Cao, Z. *Adv. Mater.* 2010, 22, 920.
[38] Weinhart, M.; Grunwald, I.; Wyszogrodzka, M.; Gaetjen, L.; Hartwig, A.; Haag, R. *Chem. Asian J.* 2010, 5, 1992.
[39] Gumbiner, B. M. *Cell* 1996, 84, 345.
[40] Ratner, B. D. *J. Dent. Educ.* 2001, 65, 1340.
[41] Lis, H.; Sharon, N. *Chem. Rev.* 1998, 98, 637.
[42] Kalb, A. J.; Levitzki, A. *Biochem. 1* 1968, 109, 669.
[43] Wood, T. K. *Environ. Microbiol.* 2009, 11, 1.
[44] Firon, N.; Duksin, D.; Sharon, N. *FEMS Microbiol. Lett.* 1985, 27, 161.
[45] Waksman, G.; Hultgren, S. J. *Nat. Rev. Microbiol.* 2009, 7, 765.
[46] Flemming, H.-C.; Wingender, J.; Szewzyk, U.; Steinberg, P.; Rice, S. A.; Kjelleberg, S. *Nat. Rev. Microbiol.* 2016, 14, 563.
[47] Halan, B.; Buehler, K.; Schmid, A. *Trends Biotechnol.* 2012, 30, 453.
[48] Russell, T. P. *Curr. Opin. Colloid Interface Sci.* 1996, 1, 107.

The invention claimed is:
1. An amphiphilic block copolymer comprising:
a first block consisting of a polymeric hydrophilic domain, wherein the polymeric hydrophilic domain consists of a polyglycerol,
an optional second block consisting of a hydrophobic domain and a first linker domain, wherein the second block is covalently bound to the first block via the first linker domain, wherein the hydrophobic domain is chosen from the group consisting of aromatic residues having 3 to 20 carbon atoms, aliphatic residues having 3 to 20 carbon atoms, oligo(dimethylsiloxane), and poly(dimethylsiloxane), an optional third block consisting of a catechol domain and a second linker domain, wherein the third block is covalently bound to the first block via the second linker domain, wherein the catechol domain comprises at least one catechol residue, and a fourth block consisting of a crosslinking domain and a third linker domain, wherein the fourth block is covalently bound to the first block via the third linker domain, wherein the crosslinking domain comprises a reactive residue enabling a crosslinking between individual molecules of the amphiphilic block copolymer, wherein the reactive residue is at least one residue chosen from the group consisting of amines, thiols, allyls, vinyls, azides, alkynes, carboxyls, anhydrides, aldehydes, and benzophenone, wherein the second block and the third block are only optional if the reactive residue of the fourth block is a benzophenone.

2. The amphiphilic block copolymer according to claim 1, wherein the block copolymer only comprises the first block and the fourth block.

3. The amphiphilic block copolymer according to claim 1, wherein in the reactive residue of the fourth block is a benzophenone.

4. The amphiphilic block copolymer according to claim 1, in wherein the block copolymer comprises the first block, the second block, the third block, and the fourth block.

5. The amphiphilic block copolymer according to claim 1, wherein the first linker domain and/or the second linker domain and/or the third linker domain is an alkane having 1 to 20 carbon atoms, wherein a hydrocarbon chain of the alkane can be interrupted by one or more oxygen, nitrogen and/or sulfur atoms and/or can be substituted by a group comprising one or more oxygen, nitrogen and/or sulfur atoms.

6. The amphiphilic block copolymer according to claim 1, wherein it comprises 1 to 20 second blocks and 1 to 20 third blocks.

7. The amphiphilic block copolymer according to claim 1, wherein a ratio between the number of hydrophilic monomers of the hydrophilic domain and the number of hydrophobic domains is between 10:1 and 100:1.

8. The amphiphilic block copolymer according to claim 1, wherein it comprises a functional domain covalently bound to the hydrophobic domain, wherein the functional domain comprises a functional group that facilitates chemical reactions of the hydrophilic domain.

9. A coating arrangement comprising a substrate and an amphiphilic block copolymer according to claim 1 bonded onto a surface of the substrate.

10. The coating arrangement according to claim 9, wherein the amphiphilic block copolymer is bonded to the surface of the substrate in form of a monolayer.

11. The coating arrangement according to claim 9, wherein the amphiphilic block copolymer is bonded to the surface of the substrate by different types of bonds at the same time.

12. The coating arrangement according to claim 9, wherein the substrate comprises at least one material chosen from the group consisting of metals, metal alloys, metal oxides, glass, $SiO_2$, graphene, and polymers.

13. The coating arrangement according to claim 9, wherein the substrate comprises a material that is coated by hydrophobic compounds.

* * * * *